(12) United States Patent
Kloss et al.

(10) Patent No.: US 12,263,220 B2
(45) Date of Patent: Apr. 1, 2025

(54) COMPOSITIONS AND METHODS FOR IMMUNOTHERAPY

(71) Applicant: MEMORIAL SLOAN-KETTERING CANCER CENTER, New York, NY (US)

(72) Inventors: Christopher C. Kloss, Phillladelphia, PA (US); Michel Sadelain, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 18/333,753

(22) Filed: Jun. 13, 2023

(65) Prior Publication Data

US 2024/0091353 A1    Mar. 21, 2024

Related U.S. Application Data

(60) Continuation of application No. 16/847,059, filed on Apr. 13, 2020, now Pat. No. 11,712,469, which is a division of application No. 14/676,255, filed on Apr. 1, 2015, now Pat. No. 10,654,928, which is a continuation of application No. PCT/US2013/063097, filed on Oct. 2, 2013.

(60) Provisional application No. 61/709,072, filed on Oct. 2, 2012.

(51) Int. Cl.
| | |
|---|---|
| A61K 39/395 | (2006.01) |
| A61K 39/00 | (2006.01) |
| A61K 39/44 | (2006.01) |
| C07K 14/705 | (2006.01) |
| C07K 14/725 | (2006.01) |
| C07K 16/28 | (2006.01) |
| C07K 16/30 | (2006.01) |
| C12N 5/0783 | (2010.01) |
| C12N 9/24 | (2006.01) |

(52) U.S. Cl.
CPC .... *A61K 39/39558* (2013.01); *A61K 39/0011* (2013.01); *A61K 39/001102* (2018.08); *A61K 39/001106* (2018.08); *A61K 39/001109* (2018.08); *A61K 39/001113* (2018.08); *A61K 39/001114* (2018.08); *A61K 39/001117* (2018.08); *A61K 39/001119* (2018.08); *A61K 39/001124* (2018.08); *A61K 39/001128* (2018.08); *A61K 39/001129* (2018.08); *A61K 39/001153* (2018.08); *A61K 39/001157* (2018.08); *A61K 39/001166* (2018.08); *A61K 39/001168* (2018.08); *A61K 39/00117* (2018.08); *A61K 39/001171* (2018.08); *A61K 39/00118* (2018.08); *A61K 39/001182* (2018.08); *A61K 39/001186* (2018.08); *A61K 39/001188* (2018.08); *A61K 39/001193* (2018.08); *A61K 39/001195* (2018.08); *A61K 39/44* (2013.01); *A61K 39/4611* (2023.05); *A61K 39/464493* (2023.05); *A61K 39/464495* (2023.05); *C07K 14/705* (2013.01); *C07K 14/70503* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 16/2809* (2013.01); *C07K 16/30* (2013.01); *C07K 16/3069* (2013.01); *C12N 5/0638* (2013.01); *C12N 9/2402* (2013.01); *C07K 2317/31* (2013.01); *C07K 2317/622* (2013.01); *C07K 2317/74* (2013.01); *C07K 2317/92* (2013.01); *C07K 2319/33* (2013.01); *C07K 2319/74* (2013.01); *C12N 2510/00* (2013.01); *C12N 2999/002* (2013.01)

(58) Field of Classification Search
None
See application file for complete search history.

(56) References Cited

U.S. PATENT DOCUMENTS

| | | | |
|---|---|---|---|
| 5,712,149 A | 1/1998 | Roberts | |
| 2004/0043401 A1 | 3/2004 | Sadelain et al. | |
| 2007/0166327 A1 | 7/2007 | Cooper et al. | |
| 2010/0178276 A1* | 7/2010 | Sadelain | A61P 31/16 435/325 |
| 2014/0099309 A1 | 4/2014 | Powell, Jr. et al. | |
| 2014/0134720 A1* | 5/2014 | Stauss | C12N 5/0636 435/328 |

(Continued)

FOREIGN PATENT DOCUMENTS

| | | |
|---|---|---|
| JP | 2015-534828 A | 12/2015 |
| WO | WO 97/35004 A1 | 9/1997 |

(Continued)

OTHER PUBLICATIONS

Chmielewski et al. (The Journal of Immunology, 2004, 173:7647-7653) (Year: 2004).*
Wilkie et al.( J Clin Immunol (2012) 32:1059-1070) (Year: 2012).*
Roitt et al., Immunology, pp. 110-111 (2000) [with English translation].

(Continued)

*Primary Examiner* — Amy E Juedes
*Assistant Examiner* — Brian Hartnett
(74) *Attorney, Agent, or Firm* — Baker Botts L.L.P.

(57) ABSTRACT

The present invention provides immunoresponsive cells, including T cells, cytotoxic T cells, regulatory T cells, and Natural Killer (NK) cells, expressing at least one of an antigen recognizing receptor and one of a chimeric costimulatory receptor. Methods of using the immunoresponsive cell include those for the treatment of neoplasia and other pathologies where an increase in an antigen-specific immune response is desired.

18 Claims, 17 Drawing Sheets

Specification includes a Sequence Listing.

(56) References Cited

U.S. PATENT DOCUMENTS

2014/0219975 A1    8/2014   June et al.
2015/0342993 A1   12/2015   Kloss et al.

FOREIGN PATENT DOCUMENTS

| WO | WO 2008/121420 A1 | 10/2008 |
| --- | --- | --- |
| WO | WO 2012/109624 A2 | 8/2012 |
| WO | WO 2012/156747 A1 | 11/2012 |
| WO | WO 2014/124143 A1 | 8/2014 |
| WO | WO 2014/145252 A2 | 9/2014 |

OTHER PUBLICATIONS

U.S. Appl. No. 16/847,059 (2020/0317781), filed Apr. 13, 2020 (Oct. 8, 2020).
U.S. Appl. No. 14/676,255 (U.S. Pat. No. 10,654,928), filed Apr. 1, 2015 (May 19, 2020).
U.S. Appl. No. 16/847,059, Jun. 13, 2023 Issue Fee Payment.
U.S. Appl. No. 16/847,059, Mar. 15, 2023 Notice of Allowance.
U.S. Appl. No. 16/847,059, Dec. 13, 2022 Response to Restriction Requirement.
U.S. Appl. No. 16/847,059, Aug. 16, 2022 Restriction Requirement.
U.S. Appl. No. 14/676,255, Jul. 14, 2016 Restriction Requirement.
U.S. Appl. No. 14/676,255, Oct. 14, 2016 Response to Restriction Requirement.
U.S. Appl. No. 14/676,255, Nov. 14, 2016 Non-Final Office Action.
U.S. Appl. No. 14/676,255, May 15, 2017 Response to Non-Final Office Action.
U.S. Appl. No. 14/676,255, Jul. 13, 2017 Final Office Action.
U.S. Appl. No. 14/676,255, Nov. 13, 2017 Response to Final Office Action.
U.S. Appl. No. 14/676,255, Nov. 28, 2017 Advisory Action.
U.S. Appl. No. 14/676,255, Dec. 11, 2017 Amendment with RCE.
U.S. Appl. No. 14/676,255, Jan. 11, 2018 Non-Final Office Action.
U.S. Appl. No. 14/676,255, Apr. 11, 2018 Response to Non-Final Office Action.
U.S. Appl. No. 14/676,255, Aug. 1, 2018 Final Office Action.
U.S. Appl. No. 14/676,255, Sep. 25, 2018 Amendment with RCE.
U.S. Appl. No. 14/676,255, Oct. 10, 2018 Advisory Action.
U.S. Appl. No. 14/676,255, Nov. 21, 2018 RCE.
U.S. Appl. No. 14/676,255, May 29, 2019 Non-Final Office Action.
U.S. Appl. No. 14/676,255, Nov. 27, 2019 Response to Non-Final Office Action.
U.S. Appl. No. 14/676,255, Dec. 11, 2019 Supplemental Response.
U.S. Appl. No. 14/676,255, Jan. 14, 2020 Notice of Allowance.
U.S. Appl. No. 14/676,255, Apr. 13, 2020 Issue Fee Payment.
Alvarez-Vallina et al. (European Journal of Immunology, 1996, 26: 2304-2309).
Brentjens et al., "Eradication of systemic B-cell tumors by genetically targeted human T lymphocytes co-stimulated by CD80 and interleukin-15," Nature Medicine 9(3):279-286 (2003).
Brentjens et al., "Safety and persistence of adoptively transferred autologous CD19-targeted T cells in patients with relapsed or chemotherapy refractory B-cell leukemias," Blood 118(18):4817-4828 (2011).
Carpenito et al., "Control of large, established tumor xenografts with genetically retargeted human T cells containing CD28 and CD137 domains," PNAS 106(9):3360-3365 (2009).
Cartellieri et al., "Chimeric Antigen Receptor-Engineered T Cells for Immunotherapy of Cancer", Journal of Biomedicine and Biotechnology 2010:956304-1 (2010).
Chicaybam et al., "Chimeric Antigen Receptors in Cancer Immuno-Gene Therapy: Current Status and Future Directions," International Reviews of Immunology 30:294-311 (2011).
Chmielewski et al., "T cell activation by antibody-like immunoreceptors: increase in affinity of the single-chain fragment domain above threshold does not increase T cell activation against antigen-positive target cells but decreases selectivity", J. Immuno., 173(12):7647-7653 (2004).
Chmielewski et al. (Gen Therapy, 2011, 18: 62-72).
Cole et al. (Journal of Immunology, 2007, 178: 5727-5734).
Curran et al., "Chimeric antigen receptors for T cell immunotherapy: current understanding and future directions", The Journal of Gene Medicine 14(6):405-415 (2012).
Di Stasi et al., (Blood, 2009, 113: 6392-6402).
Duong et al., "Enhancing the specificity of T-cell cultures for adoptive immunotherapy of cancer", Immunotherapy 3(1):33-48 (2011).
Feldmann et al. (The Prostate, 2011, 71: 998-1011).
Hanada et al., "Double or nothing on cancer immunotherapy," Nature Biotechnology 31(1):33-34 (2013).
Ho et al., "Adoptive immunotherapy: Engineering T cell responses as biologic weapons for tumor mass destruction," Cancer Cell 3:431-437 (2003).
Imai et al. (Journal of Biological Chemistry, 1997, 272: 15036-15042).
International Search Report dated Jan. 17, 2014 in International Application No. PCT/US13/63097.
Johnson et al., "Gene therapy with human and mouse T-cell receptors mediates cancer regression and targets normal tissues expressing cognate antigen," Blood 114(3):535-546 (2009).
Jorritsma et al., "Prospects and Limitations of T Cell Receptor Gene Therapy," Current Gene Therapy 11:276-287 (2011).
Kalos et al., "T Cells with Chimeric Antigen Receptors Have Potent Antitumor Effects and Can Establish Memory in Patients with Advanced Leukemia", Sci Transl Med 3(95):95ra73 (2011).
Kloss et al., "Combinatorial antigen recognition with balanced signaling promotes selective tumor eradication by engineered T cells", Nature Biotechnology 31(1):71-75 (2012).
Kochenderfer et al., "B-cell depletion and remissions of malignancy along with cytokine- associated toxicity in a clinical trial of anti-CD19 chimeric-antigen-receptor-transduced T cells," Blood 119(12):2709-2720 (2012).
Kowolik et al., "CD28 Costimulation Provided Through a CD19-Specific Chimeric Antigen Receptor Enhances In Vivo Persistence and Antitumor Efficacy of Adoptively Transferred T Cells", Cancer Research 66:10995-11004 (2006).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Lam et al., "Prostate Stem Cell Antigen Is Overexpressed in Prostate Cancer Metastases," Clin Cancer Res 11(7):2591-2596 (2005).
Liao et al., "IL-2 family cytokines: new insights into the complex roles of IL-2 as a broad regulator of T helper cell differentiation," Current Opinion in Immunology 23:598-604 (2011).
Liu et al., "Seventeen-gene signature from enriched Her2/Neu mammary tumor-initiating cells predicts clinical outcome for human HER2+:ERalpha-breast cancer," PNAS 109(15):5832-5837 (2012).
Magee et al., "Cancer Stem Cells: Impact, Heterogeneity, and Uncertainty," Cancer Cell 21:283-296 (2012).
Maher et al., "Human T-lymphocyte cytotoxicity and proliferation directed by a single chimeric TCRzeta /CD28 receptor," Nat Biotechnol. 20:70-75 (2002).
Matsui et al., "Low Affinity Interaction of Peptide-MHC Complexes with T Cell Receptors", Science 254:1788-1791 (1991).
Meyer et al., "CD44posCD49fhiCD133/2hi Defines Xenograft-Initiating Cells in Estrogen Receptor-Negative Breast Cancer," Cancer Research 70(11):4624-4633 (2010).
Morgan et al., "Case Report of a Serious Adverse Event Following the Administration of T Cells Transduced with a Chimeric Antigen Receptor Recognizing ERBB2," Molecular Therapy 18(4):843-851 (2010).
Morgenroth (The Prostate, 2007, 67: 1121-1131).
Nam et al., "Cross-linking of 4-1BB up-regulates IL-13 expression in CD8(+) T lymphocytes," Cytokine 33:87-94 (2006).
Naoto et al., "Functional design of chimeric T-cell antigen receptors for adoptive immunotherapy of cancer: architecture and outcomes", Anticancer Research Greece 32(6):2377-2383 (2012).
Nguyen et al., "Cancer stem cells: an evolving concept," Nature Reviews. Cancer 12:133-143 (2012).

(56) References Cited

OTHER PUBLICATIONS

Olson et al., "Clinical Trials of Cancer Therapies Targeting Prostate-Specific Membrane Antigen," Reviews on Recent Clinical Trials 2:182-190 (2007).
Orlandi et al., "Cloning immunoglobulin variable domains for expression by the polymerase chain reaction," Proc. Natl. Acad. Sci. USA 86:3833-3837 (1989).
Portell et al., "Antibody Therapy for Acute Lymphoblastic Leukemia", Current Hematologic Malignancy Reports 7(2):153-159 (2012).
Pule et al. (Molecular Therapy, 2005, 12: 933-941).
Robbins et al., "Tumor Regression in Patients With Metastatic Synovial Cell Sarcoma and Melanoma Using Genetically Engineered Lymphocytes Reactive with NY-ESO-1," Journal of Clinical Oncology 29(7):917-924 (2011).
Rosenberg et al., "Adoptive cell transfer: a clinical path to effective cancer immunotherapy," Nature Reviews. Cancer 8:299-308 (2008).
Sadelain et al., "Targeting Tumours With Genetically Enhanced T Lymphocytes," Nature Reviews. Cancer 3:35-45 (2003).
Sadelain et al., "The promise and potential pitfalls of chimeric antigen receptors," Current Opinion in Immunology 21:215-223 (2009).
Saeki et al., "Prostate Stem Cell Antigen: a Jekyll and Hyde Molecule?" Clin Cancer Res 16(14):3533-3538 (2010).
Schlapschy et al. (Protein Engineering, Design & Selection, 2004, 17: 847-860).
Schwartz, "T Cell Anergy," Annu. Rev. Immunol. 21:305-334 (2003).
Shih et al., "Pathogenesis of Ovarian Cancer: Clues From Selected Overexpressed Genes," Future Oncol. 5(10):1641-1657 (2009).
Shin et al., "4-1BB triggers IL-13 production from T cells to limit the polarized, Th1-mediated inflammation," Journal of Leukocyte Biology 81:1455-1465 (2007).
Silver et al., "Prostate-specific Membrane Antigen Expression in Normal and Malignant Human Tissues," Clinical Cancer Research 3:81-85 (1997).
Smith-Jones (The Journal of Nuclear Medicine, 2003, 44: 610-617).
Stephan et al., "T cell-encoded CD80 and 4-1 BBL induce auto- and transcostimulation, resulting in potent tumor rejection," Nature Medicine 13(12):1440-1449 (2007).
Strauss et al., "Analysis of Epithelial and Mesenchymal Markers in Ovarian Cancer Reveals Phenotypic Heterogeneity and Plasticity," PloS ONE 6(1):e16186 (2011).
Supplementary Partial European Search Report dated Jun. 1, 2016 in EP Application No. 13844468.
Supplementary European Search Report dated Sep. 16, 2016 in EP Application No. 13844468.
Tammana et al., "4-1BB and CD28 Signaling Plays a Synergistic Role in Redirecting Umbilical Cord Blood T Cells Against B-Cell Malignancies," Hum Gene Ther 21:75-86 (2010).
Taylor et al., "Prostate Cancer Targeting Motifs:Expression of $\alpha v \beta 3$, Neurotensin Receptor 1, Prostate Specific Membrane Antigen, and Prostate Stem Cell Antigen in Human Prostate Cancer Cell Lines and Xenografts", Prostate 72(5):523-532 (2012).
Turtle et al., "Engineered T cells for anti-cancer therapy", Current Opinion in Immunology 24(5):633-639 (2012).
Wang et al., "Optimizing Adoptive Polyclonal T Cell Immunotherapy of Lymphomas, Using a Chimeric T Cell Receptor Possessing CD28 and CD137 Costimulatory Domains," Human Gene Therapy 18:712-725 (2007).
Watts, "TNF/TNFR Family Members in Costimulation of T Cell Responses," Annual Review of Immunology 23:23-68 (2005).
Wilkie et al., "Dual Targeting of ErbB2 and MUC1 in Breast Cancer Using Chimeric Antigen Receptors Engineered to Provide Complementary Signaling," Journal of Clinical Immunology 32:1059-1070 (2012).
Zhong et al., "Chimeric Antigen Receptors Combining 4-1 BB and CD28 Signaling Domains Augment P13kinase/AKT/Bcl-XL Activation and CD8+ T Cell-Mediated Tumor Eradication," Molecular Therapy 18(2):413-420 (2010).

\* cited by examiner

Transduction of CTLs with Different and Multiple CARs

T Cell Groups | SFG Retroviral Transduction

1. Mock — N/A 2. 19z1 — | α-CD19 – CD8 – CD3zeta | IRES | dsRED |

3. P28BB — | α-PSMA – CD28 – 4 – 1BB | IRES | hrGFP |

4. 19z1 + P28BB —
| α-CD19 – CD8 – CD3zeta | IRES | dsRED |
+
| α-PSMA – CD28 – 4 – 1BB | IRES | hrGFP |

FIG. 1C

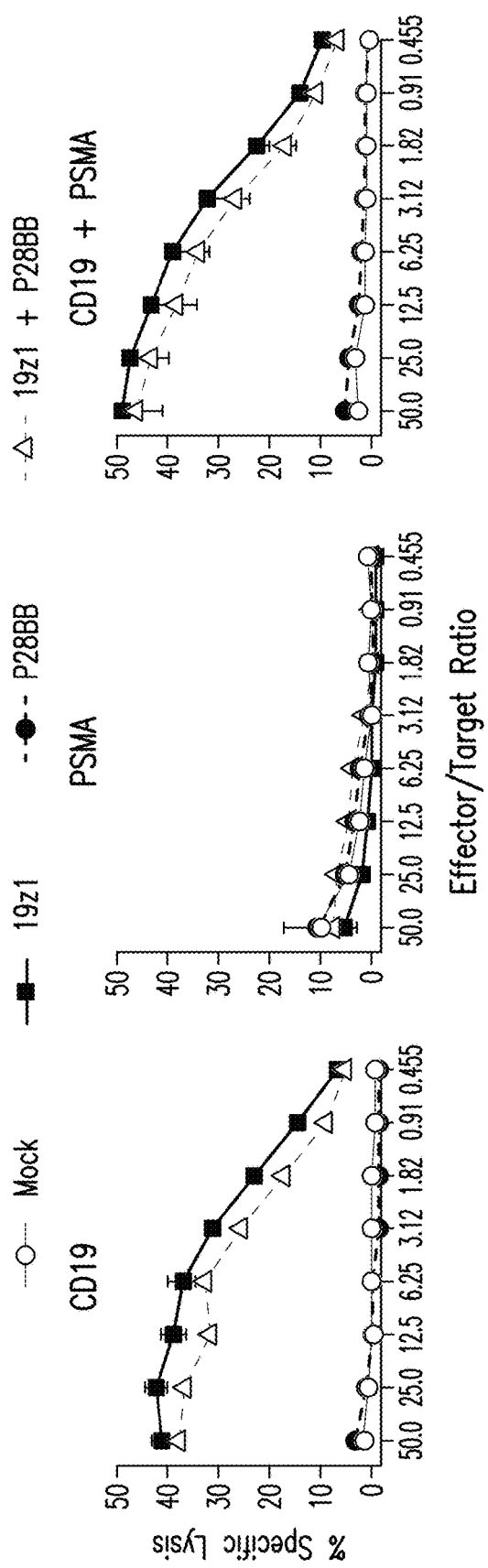
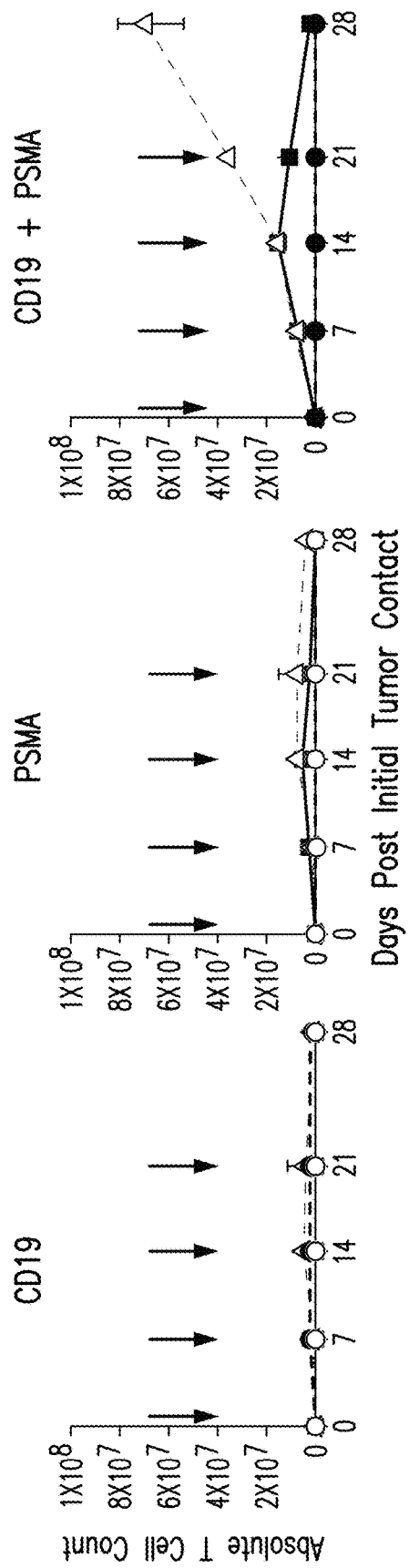
FIG. 2A
FIG. 2B

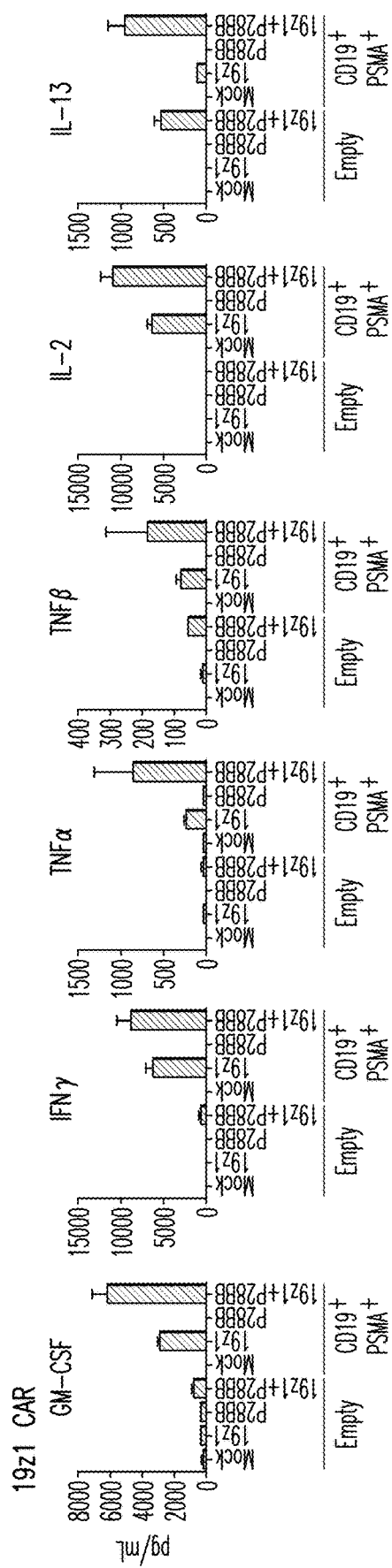
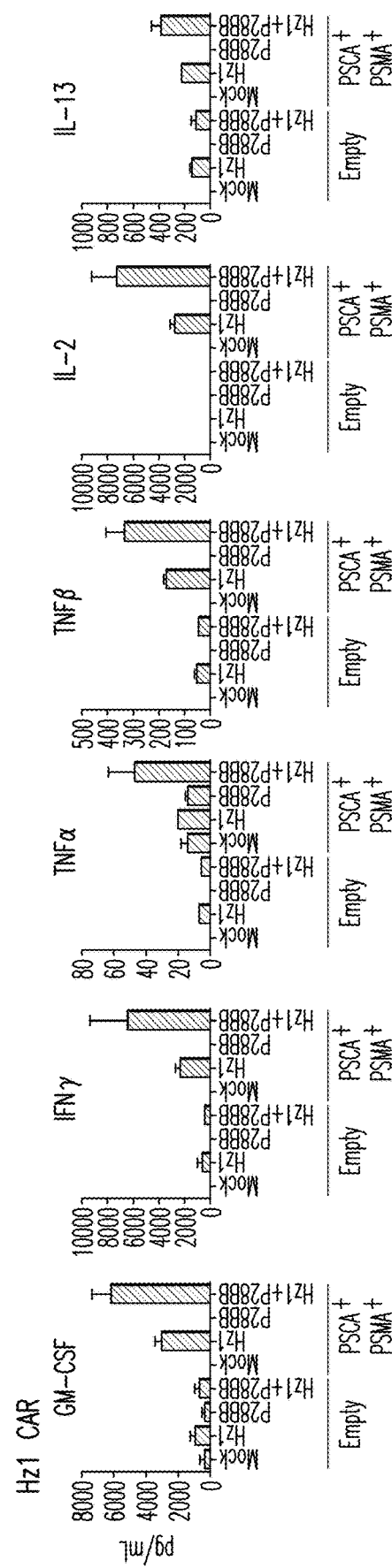
FIG. 4A
FIG. 4B

SEQUENCE LISTING

```
Sequence total quantity: 11
SEQ ID NO: 1               moltype = AA   length = 164
FEATURE                    Location/Qualifiers
source                     1..164
                           mol_type = protein
                           organism = Homo sapiens
SEQUENCE: 1
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPR                    164

SEQ ID NO: 2               moltype = AA   length = 235
FEATURE                    Location/Qualifiers
source                     1..235
                           mol_type = protein
                           organism = Homo sapiens
SEQUENCE: 2
MALPVTALLL PLALLLHAAR PSQFRVSPLD RTWNLGETVE LKCQVLLSNP TSGCSWLFQP    60
RGAAASPTFL LYLSQNKPKA AEGLDTQRFS GKRLGDTFVL TLSDFRRENE GYYFCSALSN   120
SIMYFSHFVP VFLPAKPTTT PAPRPPTPAP TIASQPLSLR PEACRPAAGG AVHTRGLDFA   180
CDIYIWAPLA GTCGVLLLSL VITLYCNHRN RRRVCKCPRP VVKSGDKPSL SARYV        235

SEQ ID NO: 3               moltype = AA   length = 220
FEATURE                    Location/Qualifiers
source                     1..220
                           mol_type = protein
                           organism = Homo sapiens
SEQUENCE: 3
MLRLLLALNL FPSIQVTGNK ILVKQSPMLV AYDNAVNLSC KYSYNLFSRE FRASLHKGLD    60
SAVEVCVVYG NYSQQLQVYS KTGFNCDGKL GNESVTFYLQ NLYVNQTDIY FCKIEVMYPP   120
PYLDNEKSNG TIIHVKGKHL CPSPLFPGPS KPFWVLVVVG GVLACYSLLV TVAFIIFWVR   180
SKRSRLLHSD YMNMTPRRPG PTRKHYQPYA PPRDFAAYRS                         220

SEQ ID NO: 4               moltype = AA   length = 255
FEATURE                    Location/Qualifiers
source                     1..255
                           mol_type = protein
                           organism = Homo sapiens
SEQUENCE: 4
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                    255

SEQ ID NO: 5               moltype = AA   length = 288
FEATURE                    Location/Qualifiers
source                     1..288
                           mol_type = protein
                           organism = Homo sapiens
SEQUENCE: 5
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CRERRRNERL RRESVRPV                288

SEQ ID NO: 6               moltype = AA   length = 182
FEATURE                    Location/Qualifiers
source                     1..182
                           mol_type = protein
                           organism = Homo sapiens
SEQUENCE: 6
MERVQPLEEN VGNAARPRFE RNKLLLVASV IGGLGLLLCF TYICLHFSAL QVSHRYPRIQ    60
SIKVQFTEYK KEKGFILTSQ KEDEIMKVQN NSVIINCDGF YLISLKGYFS QEVNISLHYQ   120
DEEPLFQLKK VRSVNSLMVA SLTYKDKVYL NYTTDNTSLD DFHVNGGELI LIHQNPGEFC   180
VL                                                                  182

SEQ ID NO: 7               moltype = AA   length = 451
FEATURE                    Location/Qualifiers
source                     1..451
                           mol_type = protein
                           organism = Homo sapiens
SEQUENCE: 7
MALPVTALLL PLALLLHAEV KLQQSGAELV RPGSSVKISC KASGYAFSSY WMNWVKQRPG    60
QGLEWIGQIY PGDGDTNYNG KFKGQATLTA DKSSSTAYMQ LSGLTSEDSA VYECARKTIS   120
SVVDFYFDYW GQGTTVTVSS GGGGSGGGGS GGGGSDIELT QSPKFMSTSV GDRVSVTCKA   180
SQNVGTNVAW YQQKPGQSPK PLIYSATYRN SGVPDRFTGS GSGTDFTLTI TNVQSKDLAD   240
```

```
YFCQQYNRYP  YTSGGGTKLE  IKRAAAPTTT  PAPRPPTPAP  TIASQPLSLR  PEACRPAAGG   300
AVHTRGLDFA  CDIYIWAPLA  GTCGVLLLSL  VITLYCNFIR  VKESRSAEPP  AYQQGQNQLY   360
NELNLGRREE  YDVLDKRRGR  DPEMGGKPRR  KNPQEGLYNE  LQKDKMAEAY  SEIGMKGERR   420
RGKGHDGLYQ  GLSTATKDTY  DALHMQALPP  R                                   451

SEQ ID NO: 8             moltype = AA  length = 478
FEATURE                  Location/Qualifiers
source                   1..478
                         mol_type = protein
                         organism = Homo sapiens
SEQUENCE: 8
MALPVTALLL  PLALLLHAEV  QLQQSGPELV  KPGTSVRISC  KTSGYTFTEY  TIHWVKQSHG   60
KSLEWIGNIN  PNNGGTTYNQ  KFEDKATLTV  DKSSSTAYME  LRSLTSEDSA  VYYCAAGWNF   120
DYWGQGTTVT  VSSGGGGSGG  GGSGGGGSDI  VMTQSHKFMS  TSVGDRVSII  CKASQDVGTA   180
VDWYQQKPGQ  SPKLLIYWAS  TRHTGVPDRF  TGSGSGTDFT  LTITNVQSED  LADYFCQQYN   240
SYPLTFGAGT  MLDLKRAAAI  EVMYPPPYLD  NEKSNGTIIH  VKGKHLCPSP  LFPGPSKPFW   300
VLVVVGGVLA  CYSLLVTVAE  IIFWVRSKRS  RLLHSDYMNM  TPRRPGPTRK  HYQPYAPPRD   360
FAAYRSRVKF  SRSADAPAYQ  QGQNQLYNEL  NLGRREEYDV  LDKRRGRDPE  MGGKPRRKNP   420
QEGLYNELQK  DKMAEAYSEI  GMKGERRRGK  GHDGLYQGLS  TATKDTYDAL  HMQALPPR     478

SEQ ID NO: 9             moltype = AA  length = 245
FEATURE                  Location/Qualifiers
source                   1..245
                         mol_type = protein
                         organism = Homo sapiens
SEQUENCE: 9
EVKLQQSGAE  LVRPGSSVKI  SCKASGYAES  SYWMNWVKQR  PGQGLEWIGQ  IYPGDGDTNY   60
NGKFKGQATL  TADKSSSTAY  MQLSGLTSED  SAVYFCARKT  ISSVVDFYFD  YWGQGTTVTV   120
SSGGGGSGGG  GSGGGGSDIE  LTQSPKFMST  SVGDRVSVTC  KASQNVGTNV  AWYQQKPGQS   180
PKPLIYSATY  RNSGVPDRET  GSGSGTDFTL  TITNVQSKDL  ADYFCQQYNR  YPYTSGGGTK   240
LEIKR                                                                   245

SEQ ID NO: 10            moltype = AA  length = 257
FEATURE                  Location/Qualifiers
source                   1..257
                         mol_type = protein
                         organism = Homo sapiens
SEQUENCE: 10
MMALPVTALL  LPLALLLHAE  VQLQQSGPEL  VKPGTSVRIS  CKTSGYTFTE  YTIHWVKQSH   60
GKSLEWIGNI  NPNNGGTTYN  QKFEDKATLT  VDKSSSTAYM  ELRSLTSEDS  AVYYCAAGWN   120
FDYWGQGTTV  TVSSGGGGSG  GGGSGGGGSD  IVMTQSHKFM  STSVGDRVSI  ICKASQDVGT   180
AVDWYQQKPG  QSPKLLIYWA  STRHTGVPDR  FTGSGSGTDF  TLTITNVQSE  DLADYFCQQY   240
NSYPLTFGAG  TMLDLKR                                                     257

SEQ ID NO: 11            moltype = AA  length = 412
FEATURE                  Location/Qualifiers
source                   1..412
                         mol_type = protein
                         organism = Homo sapiens
SEQUENCE: 11
MALPVTALLL  PLALLLHAEV  QLQQSGPELV  KPGTSVRISC  KTSGYTFTEY  TIHWVKQSHG   60
KSLEWIGNIN  PNNGGTTYNQ  KFEDKATLTV  DKSSSTAYME  LRSLTSEDSA  VYYCAAGWNF   120
DYWGQGTTVT  VSSGGGGSGG  GGSGGGGSDI  VMTQSHKFMS  TSVGDRVSII  CKASQDVGTA   180
VDWYQQKPGQ  SPKLLIYWAS  TRHTGVPDRF  TGSGSGTDFT  LTITNVQSED  LADYFCQQYN   240
SYPLTFGAGT  MLDLKRAAAI  EVMYPPPYLD  NEKSNGTIIH  VKGKHLCPSP  LFPGPSKPFW   300
VLVVVGGVLA  CYSLLVTVAF  IIFWVRSKRS  RLLHSDYMNM  TPRRPGPTRK  HYQPYAPPRD   360
FAAYRSRFSV  VKRGRKKLLY  IFKQPFMRPV  QTTQEEDGCS  CRFPEEEEGG  CE           412
```

COMPOSITIONS AND METHODS FOR IMMUNOTHERAPY

CROSS-REFERENCE TO RELATED APPLICATIONS

This application is a Continuation application of U.S. patent application Ser. No. 16/847,059, filed on Apr. 13, 2020 (now allowed), which is a Divisional application of U.S. patent application Ser. No. 14/676,255, filed on Apr. 1, 2015, now issued as U.S. Pat. No. 10,654,928, which is a Continuation application of International Patent Application No. PCT/US2013/063097, filed on Oct. 2, 2013, which claims priority to U.S. Provisional Patent Application No. 61/709,072, filed on Oct. 2, 2012, the contents of each of which are incorporated by reference in their entirety, and to each of which priority is claimed.

SEQUENCE LISTING

The specification further incorporates by reference the Sequence Listing submitted herewith via Patent Center on Jun. 13, 2023. Pursuant to 37 C.F.R. § 1.821-1.825, the Sequence Listing file, identified as 089333.0500.xml, is 13,581 bytes and was created on Jun. 12, 2023. The Sequence Listing, electronically filed herewith, does not extend beyond the scope of the specification and thus does not contain new matter.

BACKGROUND OF THE INVENTION

Prostate cancer is the most frequent cancer in males in the United States and the cause of nearly 31,000 deaths per year. When diagnosed early, cancer can be effectively treated by surgery or radiation. Postsurgical residual disease requires radiation and/or hormonal therapy, which may prevent tumor progression and metastasis. At present, there is no curative treatment for hormone refractory, metastatic prostate cancer. Immunotherapy is a targeted therapy that in principle provides for the treatment of such cancers.

Targeted T cell therapies utilizing genetically modified autologous T cells are beginning to show evidence of therapeutic efficacy in melanoma and indolent B cell malignancies. Current T cell engineering strategies retarget patient T cells to tumor antigens through a transduced T cell receptor (TCR) or a chimeric antigen receptor (CAR). The newfound ability to induce potent immune responses, however, commands the need to confine immune attacks to the tumor and avoid reactions against normal tissues that may express the targeted antigen. Alas, the limited availability of truly tumor-restricted antigens often precludes achieving highly specific targeting is the limited availability of truly tumor-restricted antigens. Accordingly, new methods of treating neoplasia are urgently required.

SUMMARY OF THE INVENTION

The present invention generally provides immunoresponsive cells, including T cells and Natural Killer (NK) cells, expressing an antigen binding receptor (e.g., CAR or TCR) having immune cell activating activity and a chimeric co-stimulating receptor (CCR), and methods of use therefore for the treatment of neoplasia, infectious disease, and other pathologies.

In one aspect, the invention provides an isolated immunoresponsive cell having an antigen recognizing receptor that binds a first antigen with low affinity, where the binding activates the immunoresponsive cell, and a chimeric co-stimulating receptor (CCR) that binds a second antigen and stimulates the immunoresponsive cell.

In another aspect, the invention provides a method of inducing tumor cell death in a subject, the method comprising administering an effective amount of an immunoresponsive cell comprising an antigen recognizing receptor that binds a first antigen with low affinity, where the binding activates the immunoresponsive cell, and a chimeric co-stimulating receptor (CCR) that binds a second antigen and stimulates the immunoresponsive cell, thereby inducing tumor cell death in the subject.

In still another aspect, the invention provides a method of treating or preventing a neoplasia in a subject, the method comprising administering an effective amount of an immunoresponsive cell comprising an antigen recognizing receptor that binds a first antigen with low affinity, where the binding activates the immunoresponsive cell, and a chimeric co-stimulating receptor (CCR) that binds a second antigen and stimulates the immunoresponsive cell, thereby treating or preventing a neoplasia in the subject.

In yet another aspect, the invention provides a method of treating prostate cancer in a subject in need thereof, the method comprising administering to the subject a therapeutically effective amount of a T cell comprising an antigen recognizing receptor that binds PSCA or CD19 with low affinity, where the binding activates the immunoresponsive cell, and a chimeric co-stimulating receptor (CCR) that binds PSMA and stimulates the immunoresponsive cell, thereby treating prostate cancer in the subject.

In still another, the invention provides a method for producing an antigen-specific immunoresponsive cell, the method involving introducing into the immunoresponsive cell a nucleic acid sequence that encodes a chimeric co-stimulating receptor (CCR), where the chimeric co-stimulating receptor has an antigen-binding domain coupled to an intracellular signaling domain that stimulates an immunoresponsive cell, where the immunoresponsive cell has an antigen recognizing receptor that binds a first antigen with low affinity, wherein the binding activates the immunoresponsive cell.

In a related aspect, the invention provides a pharmaceutical composition comprising an effective amount of an immunoresponsive cell of the invention (e.g., a tumor antigen-specific T cell in a pharmaceutical composition for the treatment of neoplasia) in a pharmaceutically acceptable excipient.

In an additional aspect, the invention provides a kit for treatment of a neoplasia, pathogen infection, an autoimmune disorder, or an allogeneic transplant, the kit containing an immunoresponsive cell having an antigen recognizing receptor that binds a first antigen and activates the immunoresponsive cell, and a chimeric co-stimulating receptor (CCR) that binds a second viral antigen and stimulates the immunoresponsive cell. The kit may further comprise written instructions for using the immunoresponsive cell for the treatment of a subject having a neoplasia, a pathogen infection, an autoimmune disorder, or an allogeneic transplant.

In various embodiments of any of the aspects delineated herein, the immunoresponsive cell is selected as having an antigen recognizing receptor with low affinity. This may involve selecting the immunoresponsive cell as having an antigen recognizing receptor that binds a first antigen with low affinity. In various embodiments of any of the aspects delineated herein, the antigen recognizing receptor is selected as having low affinity for expression in the cell. This may involve introducing a second nucleic acid sequence that encodes a chimeric antigen receptor, where the chimeric antigen receptor comprises a second antigen-binding domain coupled to a second intracellular signaling domain that activates an immunoresponsive cell. In various embodiments of any of the aspects delineated herein, the antigen recognizing receptor is a T cell receptor (TCR) or chimeric antigen receptor (CAR). In various embodiments, the intracellular signaling domain of said antigen recognizing receptor is the CD3-chain signaling domain. In various embodiments, the intracellular signaling domain of the chimeric co-stimulating receptor (CCR) is a CD97, CD11a-CD18, CD2, ICOS, CD27, CD154, CD5, OX40, 4-1BB or CD28 signaling domain.

In various embodiments of any of the aspects delineated herein, the antigen recognizing receptor is exogenous or endogenous. In various embodiments of any of the aspects delineated herein, the antigen recognizing receptor is recombinantly expressed. In various embodiments, the antigen recognizing receptor is expressed from a vector. In various embodiments, the chimeric co-stimulating receptor (CCR) is expressed from a vector. In particular embodiments, the immunoresponsive cell expresses a recombinant or an endogenous antigen receptor that is 19z1 or Pz1.

In various embodiments of any of the aspects delineated herein, the immunoresponsive cell is a T cell, a Natural Killer (NK) cell, a cytotoxic T lymphocyte (CTL), a regulatory T cell, a human embryonic stem cell, or a pluripotent stem cell from which lymphoid cells may be differentiated. In various embodiments of any of the aspects delineated herein, the immunoresponsive cell of any one of claims 1-9, where said immunoresponsive cell is autologous.

In various embodiments of any of the aspects delineated herein, the antigen is a tumor or pathogen antigen. In various embodiments of any of the aspects delineated herein, one or more antigen-binding domains are tumor antigen-binding domains. In various embodiments of any of the aspects delineated herein, the antigens or tumor antigens are selected from CAIX, CEA, CD5, CD7, CD10, CD19, CD20, CD22, CD30, CD33, CD34, CD38, CD41, CD44, CD49f, CD56, CD74, CD133, CD138, a cytomegalovirus (CMV) infected cell antigen, EGP-2, EGP-40, EpCAM, erb-B2,3,4, FBP, Fetal acetylcholine receptor, folate receptor-a, GD2, GD3, HER-2, hTERT, IL13R-a2, κ-light chain, KDR, LeY, LI cell adhesion molecule, MAGE-AI, MUC1, Mesothelin, NKG2D ligands, NY-ESO-1, oncofetal antigen (h5T4), PSCA, PSMA, ROR1, TAG-72, VEGF-R2, and WT-1. In various embodiments, the first and second antigens are selected from CD133, a cytomegalovirus (CMV) infected cell antigen, erbB2, KDR Mesothelin, NKG2D ligands, NY-ESO-1, oncofetal antigen (h5T4), PSCA, PSMA, CD19, VEGF-R2, and WT-1. In particular embodiments, the first and second antigens are selected from HER2, MUC1, CD44, CD49f, EpCAM, CEA, CD133, a cytomegalovirus (CMV) infected cell antigen, EGP-2, EGP-40, EpCAM, erb-B2,3,4, FBP, KDR, Mesothelin, NKG2D ligands, NY-ESO-1, oncofetal antigen (h5T4), PSCA, PSMA, VEGF-R2, or WT-1. In specific embodiments, the first and second antigens are selected from CD10 and CD19. In other embodiments, the first and second antigens are selected from CD56 and CD138. In certain embodiments, the first and second antigens are selected from mesothelin, folate receptor-a, CD44, and CD133.

In various embodiments of any of the aspects delineated herein, the neoplasia is selected from the group consisting of prostate cancer, breast cancer, B cell leukemia, multiple myeloma, and ovarian cancer. In various embodiments of any of the aspects delineated herein, the method reduces the number of tumor cells, reduces tumor size, and/or eradicates the tumor in the subject.

In various embodiments, the neoplasia is prostate cancer and the first and second tumor antigens are distinct antigens selected from PSCA, PSMA, CD19, CD133, a cytomegalovirus (CMV) infected cell antigen, erb-B2, KDR Mesothelin, NKG2D ligands, NY-ESO-1, oncofetal antigen (h5T4), VEGF-R2, and WT-1. In various embodiments, the neoplasia is breast cancer and the first and second tumor antigens are distinct antigens selected from HER2, MUC1, CD44, CD49f, EpCAM, CEA, CD133, a cytomegalovirus (CMV) infected cell antigen, EGP-2, EGP-40, EpCAM, erb-B2,3,4, FBP, KDR, Mesothelin, NKG2D ligands, NY-ESO-1, oncofetal antigen (h5T4), PSCA, PSMA, VEGF-R2, or WT-1. In particular embodiments, the neoplasia is B cell leukemia and the first and second tumor antigens are selected from CDIO and CD19. In certain embodiments, the neoplasia is multiple myeloma and the first and second tumor antigens are selected from CD56 and CD138. In various embodiments, the neoplasia is ovarian cancer and the first and second tumor antigens are distinct antigens selected from mesothelin, folate receptor-a, CD44, and CD133.

The invention provides compositions and methods that provide for T cell targeting of tumor cells. Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

FIGS. 1A-1C are graphics depicting chimeric antigen receptor (CAR) and chimeric costimulatory receptor (CCR) vector design and expression via transduction of primary human T cells. FIG. 1A depicts generation of CARs by fusing heavy and light chains of immunoglobulin variable domains to the CD8 transmembrane domain, which is fused to the cytosolic signaling domains of CD3. By using an Internal Ribosomal Entry Site (IRES) to enable bicistronic expression, CAR expression can be easily detected by correlation to dsRED fluorescence (data not shown). The CCR was generated by fusing an scFv to a CD28 transmembrane and signaling domain[15], fused to a 4-1BB (aka CD137) cytosolic signaling domain.[21] CCR expression can be correlated to the bicistronic expression of hrGFP (data not shown). Abbreviations: LTR—Long Terminal Repeat; SD— Splice Donor site; SA—Splice Acceptor site; VH—or $V_L$— Variable Heavy or Light domains, respectively; EC—Extracellular domain; TM—Transmembrane domain; C—Cytosolic domain; IRES—Internal Ribosomal Entry Site; dsRED—*Discosoma* sp. Red fluorescent protein, hrGFP—Human Recombinant Green Fluorescent Protein. FIG. 1B depicts representative transduction efficiencies of primary human T cells using these retroviral vectors. FIG. 1C depicts transduction of CTLs with different and multiple CARs for the present studies.

FIGS. 2A-2D show that dual-receptor, CAR/CCR-mediated activation of human T cells allowed for robust CTL function, long-term proliferation, and enhanced tumor eradication upon binding of two antigens. FIG. 2A shows that T cells expressing chimeric receptors lysed cells positive for antigen when the CAR specific to CD19 is expressed by T cells in CTL assays, compared to untransduced or P28BB transduced T cells. Plots are representative of n>4 experiments, with error bars representing standard deviation of the mean of 3 replicates. FIG. 2B shows long-term proliferation of T cells by absolute T cell counts over 31 days of T cells expressing none, one, or both chimeric receptors that were co-cultured with human tumor cell lines expressing both or either antigen alone. Arrows indicate re-stimulation of T cells using freshly irradiated tumor cells. Only when dual-receptor expressing T cells encounter both antigens is robust long-term proliferation observed. Plots are representative of n>4 experiments with error bars representing standard deviation of the mean of 3 replicates. FIG. 2C depicts the efficacy of systemic tumor eradication by tumor-sensing T (TTS) cells assessed by infusing $1.0 \times 10^6$ T cells intravenously (IV) into NSG mice bearing luciferase expressing $CD19^+PSMA^+PC3$ human prostate tumor. Tumor burden was quantitatively measured weekly by using BLI. Images of two representative mice from each group are shown with the pixel intensity from the luminescence of tumors represented in color. An average of tumor burden was plotted with error bars representing standard deviation from the mean of values from 6 mice per group. FIG. 2D depicts selective eradication of DP tumors using a tri-tumor mouse model by subcutaneously injecting $1 \times 10^6$ PC3 tumors cells each of cells positive for CD19 alone into the left flanks, cells positive for PSMA alone into the right flanks, and cells positive for both CD19 and PSMA into the backs of the mice. T cells expressing either 19z1, P28BB, or both 19z1+P28BB of the chimeric receptors were infused intravenously 7 days post tumor infusion. Representative images of 2 mice per group bearing these tumors are shown with luminescence of tumors represented in color. Tumors were quantitatively measured using calipers and tumor volumes were plotted versus time for each tumor. Error bars represent standard deviation from the mean of 6 mice. Statistical significance was determined using two-tailed unpaired t tests to compare values obtained from 19z1 T cells and 19z1+P28BB T cells and p values are represented as * for <0.05 or ** for <0.01.

FIG. 3A depicts the evaluation of three different scFvs specific to PSCA for their assembly into bispecific antibodies that contain specificity for CD3 as well. T cells were co-cultured at ratio of 20:1 with $PSCA^+PC3$ tumor cells and antibodies added at varying amounts and specific lysis was measured. FIG. 3B depicts generation of CARs using the anti-PSCA scFvs that display varied efficacy in cytotoxicity assays. The CAR mediated specific lysis of target cells expressing PSCA corroborated the reduced efficacy of the Lzl scFv by requiring a 50 fold high effector: target ratio to achieve the same level of lysis of that for either HzI or MzI. FIGS. 3C and 3D depict selective eradication of systemic prostate tumors expressing PSCA and PSMA was investigated by using these inefficient scFvs. Tumors (FIG. 5) were established and treated as described in FIGS. 2A-2D. After 14 days, $1.0 \times 10^6$ chimeric receptor positive T cells for MzI+P28BB (FIG. 3C) or LzI+P28BB (FIG. 3D) were infused intravenously. Images of two representative mice from each group are shown with luminescence from tumors represented in color (from Blue=$5 \times 10^5$ to Red=$2 \times 10^7$ photons). The average tumor burden was quantified by luminescence and plotted with error bars representing standard deviation from the mean of values from 5 mice per group. Two mice that received PSMA tumor (green line) died after day 49 and therefore the mean value for luminescence was averaged from 3 values for days 56 and 63. FIG. 3E Selective antitumor responses to only $PSCA^+PSMA^+$ tumors was achieved by LzI+P28BB T cells in mice that also had $PSCA^+PSMA^+$ and $PSCA^+PSMA^-$ tumors, similar to FIG. 2D. Statistical significance was determined using two-tailed unpaired t tests to compare values obtained from LzI T cells and LzI+P28BB T cells and p values are represented as * for <0.05 or ** for <0.01.

FIGS. 4A-4D depict enhanced cytokine secretion and BclxL expression is found by TTS cells when co-cultured on DP tumors. FIG. 4A depicts multiplex cytokine analysis of untransduced T cells or T cells transduced with 19z1, P28BB, or both 48 hours post first antigen stimulation using either untransduced PC3 cells (Empty) or $CD19^+PSMA^+$ PC3 cells. Error bars represent standard deviation from the mean of 2 biological replicates. FIGS. 4B-4D depict multiplex cytokine analysis of untransduced T cells or T cells transduced with Hz] (FIG. 4B), MzI (FIG. 4C), and LzI (FIG. 4D) anti-PSCA CARs, P28BB CCRs, or both CAR+CCR is shown 48 hours post second antigen stimulation using either Empty or PSCA+PSMA+PC3 cells.

FIG. 6A depicts that TTS cells expressing an efficient CAR, become potently stimulated by $A^+113^+$ cells to facilitate immune response against $A^+$ cells. $CAR^+CCR^+$ cells can bind tumor antigen $A^+$ cells with a CAR that supplies CD3 activation signals. This can result in short-term cell lysis. $CAR^+CCR^+$ cells can bind tumor antigen $B^+$ cells with a CCR that supplies CD28 and CD137 signals. This signal alone is not sufficient to induce lysis or proliferation. Only when $CAR^+CCR^+$ cells bind tumor antigen $A^+B^+$ cells with a CAR and CCR can both activation and stimulation be provided. This results in robust lysis, T cell proliferation, enhanced cytokine secretion, upregulation of BclxL, and the ability to selectively eradicate tumors in vivo. However, depending on the efficacy of the CAR, these $CAR^+CCR^+$ cells can potentially recirculate to lyse cells single positive for antigen specific to the CAR. FIG. 6B depicts that by reducing the efficacy of the CAR, TT's cells can be functionally rescued by CCR binding when $A^+B^+$ cells are encountered to selectively respond and eradicate $A^+13^+$ cells, while avoiding response to A+ cells. FIG. 6C shows that by co-expressing one CAR that supplies a TCR activation signal upon binding a tumor antigen and a second CAR that supplies stimulation signals upon binding a different tumor antigen, T lymphocytes will only eradicate tumors expressing both antigens, but not tumors expressing either antigen alone.

DETAILED DESCRIPTION OF THE INVENTION

Figure 1A:
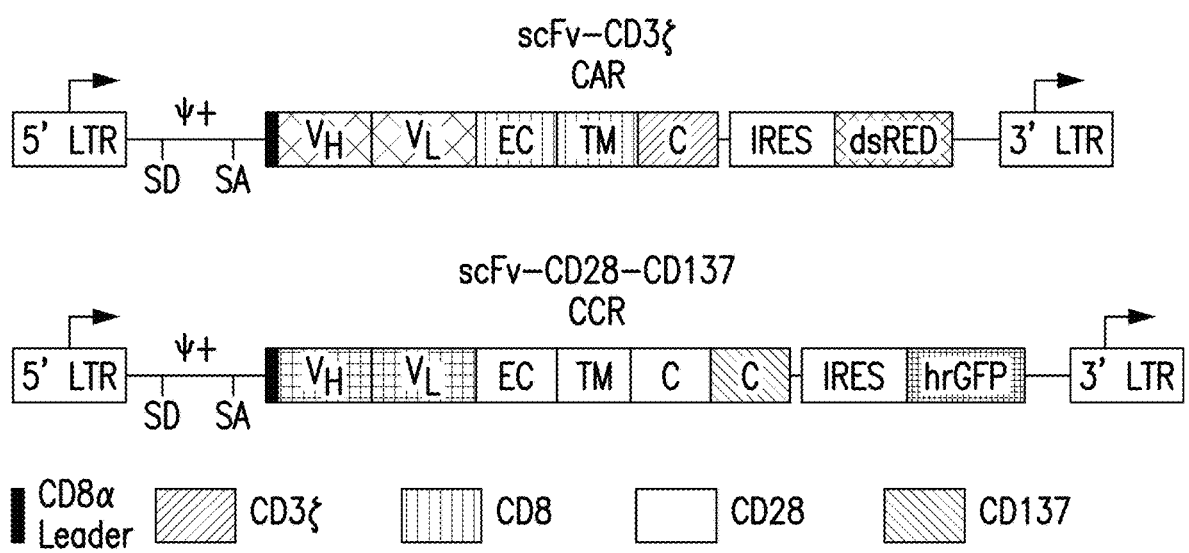

All patents, published applications and other references mentioned in this specification are herein incorporated by reference into the present disclosure.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds antigen, a formation of an immunological synapse occurs that includes clustering of many molecules near the bound receptor (e.g. CD4 or CD8, CD3///, etc.) This clustering of membrane bound signaling molecules allows for ITAM motifs contained within the CD3 chains to become phosphorylated. This phosphorylation in turn initiates a T cell activation pathway ultimately activating transcription factors, such as NF-KB and AP-1. These transcription factors induce global gene expression of the T cell to increase IL-2 production for proliferation and express master regulator T cell proteins in order to initiate a T cell mediated immune response. By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), 0X40, and ICOS. Without being bound to a particular theory, receiving multiple stimulatory signals is important to mount a robust and long-term T cell mediated immune response. Without receiving these stimulatory signals, T cells quickly become inhibited and unresponsive to antigen. While the effects of these co-stimulatory signals vary and remain partially understood, they generally result in increasing gene expression in order to generate long lived, proliferative, and anti-apoptotic T cells that robustly respond to antigen for complete and sustained eradication.

The term "antigen recognizing receptor" as used herein refers to a receptor that is capable of activating an immune cell (e.g., a T-cell) in response to antigen binding. Exemplary antigen recognizing receptors may be native or endogenous T cell receptors or chimeric antigen receptors in which a tumor antigen-binding domain is fused to an intracellular signaling domain capable of activating activating an immune cell (e.g., a T-cell). In various embodiments, an antigen recognizing receptor is selected to have low or minimal affinity or avidity for the antigen.

By "affinity" is meant a measure of the binding strength between antibody and a simple hapten or antigen determinant. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, including use of binding experiments to calculate affinity. In the case of an antibody (Ab) binding to an antigen (Ag), the affinity constant is used (expressed as inverted dissociation constant).

$$Ab + Ag = AbAg$$

$$K_a = \frac{[AbAg]}{[Ab][Ag]K_a} = 1$$

The chemical equilibrium of antibody binding is also the ratio of the on-rate (k forward) and off-rate$_{(kback)}$ constants. Two antibodies can have the same affinity, but one may have both a high on- and off-rate constant, while the other may have both a low on- and off-rate constant.

$$K_a = \frac{k\text{forward}}{k\text{back}} = \frac{\text{on-rate}}{\text{off-rate}}$$

Antibody activity in functional assays (e.g., cell lysis assay) is also reflective of antibody affinity. In various embodiments of the invention, the antigen recognizing receptor has low affinity. Low affinity includes micromolar and nanomolar affinities (e.g. $10^{-5}$, $50^{-6}$, $10^{-6}$, $5 \times 10^{-7}$, $10^{-7}$, $5 \times 10^{-8}$, $10^{-8}$, $5 \times 10^{-9}$, $10^{-9}$ M). Antibody and affinities can be phenotypically characterized and compared using functional assay (e.g., cell lysis assay).

By "affinity" is meant a measure of the binding strength between antibody and a simple The term "chimeric co-stimulatory receptor" (CCR), as used herein refers to a specific type of chimeric antigen receptor (CAR) that mediates costimulation independently of activation. When expressed on immunoresponsive cells in combination with an antigen recognizing receptor (e.g., CAR or TCR that activates the cell), the CCR is targeted to a second antigen. In certain embodiments, the CCR has mid or high affinity for its target antigen.

The term "chimeric antigen receptor" (CAR) as used herein refers to a tumor antigen-binding domain that is fused to an intracellular signaling domain capable of activating or stimulating T cells. Most commonly, the CAR's extracellular binding domain is composed of a single chain variable fragment (scFv) derived from fusing the variable heavy and light regions of a murine or humanized monoclonal antibody. Alternatively, scFv's may be used that are derived from Fab's (instead of from an antibody, e.g., obtained from Fab libraries). In various embodiments, this scFv is fused to a transmembrane domain and then to intracellular signaling domain. "First-generation" CARs include those that solely provide CD3 signals upon antigen binding, "Second-generation" CARs include those that provide both costimulation (e.g. CD28 or CD137) and activation (CD3). "Third-generation" CARs include those that provide multiple costimulation (e.g. CD28 and CD137) and activation (CD3). In CAR applications to date, the CAR is selected to have high affinity or avidity for the antigen, which is distinct and distinguishable from the invention described herein.

By "CD3 polypeptide" is meant a protein having at least 85, 90, 95, 96, 97, 98, 99 or 100% identity to NCBI Reference No: NP_932170 or a fragment thereof that has activating or stimulatory activity. An exemplary CD3 is provided in Table 1 below. By "CD3 nucleic acid molecule" is meant a polynucleotide encoding a CD3 polypeptide.

By "CD8 polypeptide" is meant a protein having at least 85, 90, 95, 96, 97, 98, 99 or 100% identity to NCBI Reference No: NP_001759 or a fragment thereof that has stimulatory activity. An exemplary CD8 is provided in Table 1 below. By "CD8 nucleic acid molecule" is meant a polynucleotide encoding a CD8 polypeptide.

By "CD28 polypeptide" is meant a protein having at least 85, 90, 95, 96, 97, 98, 99 or 100% identity to NCBI Reference No: NP_006130 or a fragment thereof that has stimulatory activity. An exemplary CD28 is provided in Table 1 below. By "CD28 nucleic acid molecule" is meant a polynucleotide encoding a CD28 polypeptide.

By "4-1BB polypeptide" is meant a protein having at least 85, 90, 95, 96, 97, 98, 99 or 100% identity to NCBI Reference No: P41273 or NP_001552 or a fragment thereof that that acts as a tumor necrosis factor (TNF) ligand. An exemplary 4-1BB is provided in Table 1 below. By "4-1BBL nucleic acid molecule" is meant a polynucleotide encoding a 4-1BBL polypeptide.

By "CD80 polypeptide" is meant a protein having at least 85, 90, 95, 96, 97, 98, 99 or 100% identity to NCBI Reference No: NP_005182 or a fragment thereof that acts as an Ig superfamily ligand. An exemplary CD80 polypeptide is provided in Table 1 below.

By "CD80 nucleic acid molecule" is meant any polynucleotide encoding a CD80 polypeptide. An exemplary CD80 nucleic acid molecule is NM_005191.

By "OX4OL polypeptide" is meant a protein having at least 85, 90, 95, 96, 97, 98, 99 or 100% identity to NCBI Reference No: BAB18304 or NP_003317 or a fragment thereof that is a tumor necrosis factor (TNF) ligand. By "OX4OL nucleic acid molecule" is meant a polynucleotide encoding a OX4OL polypeptide.

By "19z1 polypeptide" is meant a protein having at least 85, 90, 95, 96, 97, 98, 99 or 100% identity to the sequence provided below and having activating activity when bound to CD19.

By "P28z polypeptide" is meant a protein having at least 85, 90, 95, 96, 97, 98, 99 or 100% identity to the sequence provided below.

By "CD19" is meant a protein having at least 85, 90, 95, 96, 97, 98, 99 or 100% identity to the sequence provided below and is able to bind CD19.

By "PSMA" is meant a protein having at least 85, 90, 95, 96, 97, 98, 99 or 100% identity to the sequence provided below and is able to bind PSMA.

By "P28BB" is meant a protein having at least 85, 90, 95, 96, 97, 98, 99 or 100% identity to the sequence provided below and having stimulatory activity when bound to PSMA.

TABLE 1

| SEQ ID NO. | Name | | | | |
|---|---|---|---|---|---|
| 1 | CD3 | mkwkalftaa | ilqaqlpite | aqsfglldpk | lcylldgilf |
| | | iygviltalf | lrvkfsrsad | apayqqgqnq | lynelnlgrr |
| | | eeydvldkrr | grdpemggkp | grrknpqegl | ynelqkdkma |
| | | eayseigmkg | errrgkghdg | lyqglsta | tkdtydalhm |
| | | qalppr | | | |
| 2 | CD8 | malpvtalll | plalllhaar | psqfrvspld | rtwnlgetve |
| | | lkcqvllsnp | tsgcswlfqp | rgaaasptfl | lylsqnkpka |
| | | aegldtqrfs | gkrlgdtfvl | tlsdfrrene | gyyfcsalsn |
| | | simyfshfvp | vflpakpttt | paprpptpap | tiasqplslr |
| | | peacrpaagg | avhtrgldfa | cdiyiwapla | gtcgvlllsl |
| | | vitlycnhrn | rrrvckcprp | vvksgdkpsl | saryv |
| 3 | CD28 | mlrlllalnl | fpsiqvtgnk | ilvkqspmlv | avdnavnlsc |
| | | kysynlfsre | fraslhkgld | savevcvvyg | nysqqlqvys |
| | | ktgfncdgkl | gnesvtfylq | nlyvnqtdiy | fckievmypp |
| | | pyldneksng | tiihvkgkhl | cpsplfpgps | kpfwvlvvvg |
| | | gvlacysllv | tvafiiifwvr | skrsrllhsd | ymnmtprrpg |
| | | ptrkhyqpya | pprdfaavrs | | |
| 4 | 4-1BB | mgnscyniva | tlllvlnfer | trslqdpcsn | cpagtfcdnn |
| | | rnqicspcpp | nsfssaggqr | tcdicrqckg | vfrtrkecss |
| | | tsnaecdctp | gfhclgagcs | mceqdckqgq | eltkkgckdc |
| | | cfgtfndqkr | gicrpwtncs | ldgksvlvng | tkerdvvcgp |
| | | spadlspgas | svtppapare | pghspqiisf | flaltstall |
| | | fllffltlrf | svvkrgrkkl | lyifkgpfmr | pvqttqeedg |
| | | cscrfpeeee | ggcel | | |
| 5 | CD80 | mghtrrqgts | pskcpylnff | qllvlaglsh | fcsgvihvtk |
| | | evkevatlsc | ghnvsveela | qtriywqkek | kmvltmmsgd |
| | | mniwpeyknr | tifditnnls | ivilalrpsd | egtyecvvlk |
| | | yekdafkreh | laevtlsvka | dfptpsisdf | eiptsnirri |
| | | icstsggfpe | phlswlenge | elnainttvs | qdpetelyav |
| | | sskidfnmtt | nhsfmcliky | ghlrvnqtfn | wnttkqehfp |
| | | dnllpswait | lisvngifvi | ccltycfapr | crerrrnerl |
| | | rresvrpv | | | |
| 6 | OX4OL | mervqpleen | vgnaarprfe | rnklllvasv | iqglllcf |
| | | tyiclhfsal | qvshrypriq | sikvqfteyk | kekgfiltsq |
| | | kedeimkvqn | nsviincdgf | ylislkgyfs | qevnislhyq |
| | | kdeeplfqlk | kvrsvnslmv | asltykdkvy | lnvttdntsl |
| | | ddfhvnggel | ilihqnpgef | cvl | |
| 7 | 19z1 | MALPVTALLLPLALLLHAEVKLQQSGAELVRPGSSVKISCKAS | | | |
| | | GYAFSSYWMNWVKQRPGQGLEWIGQIYPGDGDTNYNGKFKGQA | | | |

TABLE 1-continued

| SEQ ID NO. | Name | |
|---|---|---|
| | | TLTADKSSSTAYMQLSGLTSEDSAVYECARKTISSVVDFYFDY WGQGTTVTVSSGGGGSGGGGSGGGGSDIELTQSPKFMSTSVGD RVSVTCKASQNVGTNVAWYQQKPGQSPKPLIYSATYRNSGVPD RFTGSGSGTDFTLTITNVQSKDLADYFCQQYNRYPYTSGGGTK LEIKRAAAPTTTPAPRPPTPAPTIASQPLSLRPEACRPAAGGA VHTRGLDFACDIYIWAPLAGTCGVLLLSLVITLYCNHRVKFSR SAEPPAYQQGQNQLYNELNLGRREEYDVLDKRRGRDPEMGGKP RRKNPQEGLYNELQKDKMAEAYSEIGMKGERRRGKGHDGLYQG LSTATKDTYDALHMQALPPR |
| 8 | P28z | MALPVTALLLPLALLLHAEVQLQQSGPELVKPGTSVRISCKTSGYTF TEYTIHWVKQSHGKSLEWIGNINPNNGGTTYNQKFEDKATLTVDKSS STAYMELRSLTSEDSAVYYCAAGWNFDYWGQGTTVTVSSGGGGSGGG GSGGGGSDIVMTQSHKFMSTSVGDRVSIICKASQDVGTAVDWYQQKP GQSPKLLIYWASTRHTGVPDRFTGSGSGTDFTLTITNVQSEDLADYF CQQYNSYPLTFGAGTMLDLKRAAAIEVMYPPPYLDNEKSNGTIIHVK GKHLCPSPLFPGPSKPFWVLVVVGGVLACYSLLVTVAFIIFWVRSKR SRLLHSDYMNMTPRRPGPTRKHYQPYAPPRDFAAYRSRVKFSRSADA PAYQQGQNQLYNELNLGRREEYDVLDKRRGRDPEMGGKPRRKNPQEG LYNELQKDKMAEAYSEIGMKGERRRGKGHDGLYQGLSTATKDTYDAL HMQALPPR |
| 9 | CD19 | EVKLQQSGAELVRPGSSVKISCKASGYAFSSYWMNWVKQRPGQGLEW IGQIYPGDGDTNYNGKFKGQATLTADKSSSTAYMQLSGLTSEDSAVY FCARKTISSVVDFYFDYWGQGTTVTVSSGGGGSGGGGSGGGGSDIEL TQSPKFMSTSVGDRVSVTCKASQNVGTNVAWYQQKPGQSPKPLIYSA TYRNSGVPDRFTGSGSGTDFTLTITNVQSKDLADYFCQQYNRYPYTS GGGTKLEIKR |
| 10 | PSMA | MMALPVTALLLPLALLLHAEVQLQQSGPELVKPGTSVRISCKTSGYT FTEYTIHWVKQSHGKSLEWIGNINPNNGGTTYNQKFEDKATLTVDKS SSTAYMELRSLTSEDSAVYYCAAGWNFDYWGQGTTVTVSSGGGGSGG GGSGGGGSDIVMTQSHKFMSTSVGDRVSIICKASQDVGTAVDWYQQK PGQSPKLLIYWASTRHTGVPDRFTGSGSGTDFTLTITNVQSEDLADY FCQQYNSYPLTFGAGTMLDLKR |
| 11 | P28BB | MALPVTALLLPLALLLHAEVQLQQSGPELVKPGTSVRISCKTSGYTF TEYTIHWVKQSHGKSLEWIGNINPNNGGTTYNQKFEDKATLTVDKSS STAYMELRSLTSEDSAVYYCAAGWNFDYWGQGTTVTVSSGGGGSGGG GSGGGGSDIVMTQSHKFMSTSVGDRVSIICKASQDVGTAVDWYQQKP GQSPKLLIYWASTRHTGVPDRFTGSGSGTDFTLTITNVQSEDLADYF CQQYNSYPLTFGAGTMLDLKRAAAIEVMYPPPYLDNEKSNGTIIHVK GKHLCPSPLFPGPSKPFWVLVVVGGVLACYSLLVTVAFIIFWVRSKR SRLLHSDYMNMTPRRPGPTRKHYQPYAPPRDFAAYRSRFSVVKRGRK KLLYIFKQPFMRPVQTTQEEDGCSCRFPEEEEGGCE |

Nucleic acid molecules useful in the methods of the invention include any nucleic acid molecule that encodes a polypeptide of the invention or a fragment thereof. Such nucleic acid molecules need not be 10000 identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 3500 formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 1001.1 g/ml denatured salmon sperm DNA (ssDNA). In a most preferred embodiment, hybridization will occur at 42° C. C. in 250 mM NaCl, 25 mM trisodium citrate, 1% SDS, 50% formamide, and 200 p.g/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature.

For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42.degree C. in 15 mM NaCl, 1.5 mM trisodium citrate, and 0.1% SDS. In another embodiment, wash steps will occur at 68° C. in 15 mM NaCl, 1.5 mM trisodium citrate, and 0.1% SDS. Additional variations on these conditions will be readily apparent to those skilled in the art.

Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In particular, the ligand binds a receptor on another cell, allowing for cell-to-cell recognition.

The term "constitutive expression" as used herein refers to expression under all physiological conditions.

By "disease" is meant any condition or disorder that damages or interferes with the normal function of a cell, tissue, or organ. Examples of diseases include neoplasia or pathogen infection of cell.

By "effective amount" is meant an amount sufficient to arrest, ameliorate, or inhibit the continued proliferation, growth, or metastasis (e.g., invasion, or migration) of a neoplasia.

By "enforcing tolerance" is meant preventing the activity of self-reactive cells or immunoresponsive cells that target transplanted organs or tissues.

By "exogenous" is meant a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "tumor antigen-binding domain" as used herein refers to a domain capable of specifically binding a particular antigenic determinant or set of antigenic determinants present on a tumor.

By "modulate" is meant to alter positively or negatively. Exemplary modulations include a 1%, 2%, 5%, 10%, 25%, 50%, 75%, or 100% change.

By "neoplasia" is meant a disease characterized by the pathological proliferation of a cell or tissue and its subsequent migration to or invasion of other issues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells). Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, ligodenroglioma, schwannoma, meningioma, melanoma, neuroblastoma, and retinoblastoma). In one embodiment, screening methods of the invention identify compositions that are useful for treating breast or lung cancer.

By "receptor" is meant a polypeptide, or portion thereof, present on a cell membrane that selectively binds one or more ligands.

By "recognize" is meant selectively binds a target. A T cell that recognizes a virus typically expresses a receptor that binds an antigen expressed by the virus.

By "pathogen" is meant a virus, bacteria, fungi, parasite or protozoa capable of causing disease. Exemplary viruses include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bungs viruses, phleboviruses and Nairo viruses); Arena Viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas* species, and *Salmonella* species. Specific examples of infectious bacteria include but are not limited to, *Helicobacter pyloris, Borelia burgdoiferi, Legionella pneumophilia, Mycobacteria* sps (e.g. *M. tuberculosis, M avium, M intracellulare, M. kansaii, M. gordonae*), *Staphylococcus aureus, Neisseria gonorrhoeae, Neisseria meningitidis, Listeria monocytogenes, Streptococcus* pyo genes (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

By "specifically binds" is meant a polypeptide or fragment thereof that recognizes and binds a polypeptide of interest, but which does not substantially recognize and bind other molecules in a sample, for example, a biological sample, which naturally includes a polypeptide of the invention.

The term "tumor antigen" as used herein refers to any polypeptide expressed by a tumor that is capable of inducing an immune response.

By "virus antigen" is meant a polypeptide expressed by a virus that is capable of inducing an immune response.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

The term "subject" as used herein refers to a vertebrate, preferably a mammal, more preferably a human.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the invention are described in the following disclosure and are within the ambit of the invention.

The present invention generally provides cells, including genetically modified immunoresponsive cells (e.g., T cells, Natural Killer (NK) cells, cytotoxic T lymphocytes (CTL) cells) expressing at least a combination of an antigen-recognizing receptor (e.g., TCR or CAR) and a chimeric co-stimulating receptor (CCR), and methods of use therefore for the treatment of neoplasia and other pathologies where an increase in an antigen-specific immune response is desired. The invention is based, at least in part, on the discovery that the simultaneous engagement of two antigens co-expressed by a tumor cell by an antigen-recognizing receptor and chimeric co-stimulating receptor is useful for activating and stimulating an immunoreactive cell without systemic effects. In particular, the reactivity against tissues expressing either antigen alone is preferably minimal, inducing T cell activation in the presence of both antigens but not either one alone. T cell activation is mediated by a TCR or a CAR targeted to an antigen (e.g., CD19 or prostate stem cell antigen, PSCA). Costimulation is independently mediated by a "chimeric costimulatory receptor" (CCR),[12, 13] which is targeted to a second antigen (e.g., prostate-specific membrane antigen, PSMA). Such an approach resulted in augmented reactivity against dual-antigen positive (DP) tumors, but failed to avert enhanced reactivity against single antigen positive (SP) tumors. It was found that tumor sensing T cells could be made to differentiate DP tumors from SP tumors by attenuating T cell activation to a level where T cell activation is by itself ineffective, but functionally rescued at the tumor site by a CCR engaged by an independent, co-expressed antigen. This approach provides immunogenicity within the tumor microenvironment for tumor eradication while not affecting SP cells that are normal or non-neoplastic and represents a significant advance over conventional adoptive T cell therapy.

Furthermore, this approach is not limited to the treatment of neoplasias, but is amenable to a wide range of applications where an increase in an antigen-specific immune response is desired, such applications include not only the treatment of neoplasias, but also for the enhancement of an immune response against a pathogen infection or an infectious disease and to reinforce immune tolerance in regulatory T cells in the context of autoimmunity or allogeneic transplantation.

Hematopoietic Cell Lineages

Mammalian hematopoietic (blood) cells provide a diverse range of physiologic activities. Hematopoietic cells are divided into lymphoid, myeloid and erythroid lineages. The lymphoid lineage, comprising B, T and natural killer (NK) cells, provides for the production of antibodies, regulation of the cellular immune system, detection of foreign agents in the blood, detection of cells foreign to the host, and the like. The term "T cells" as used herein refers to lymphocytes that mature in the thymus and are chiefly responsible for cell-mediated immunity. T cells are involved in the adaptive immune system. The term "natural killer (NK) cells" as used herein refers to lymphocytes that are part of cell-mediated immunity and act during the innate immune response. They do not require prior activation in order to perform their cytotoxic effect on target cells. Cytotoxic T cells (CTL or killer T cells) are a subset of T lymphocytes capable of inducing the death of infected somatic or tumor cells.

Cells for Use in the Methods of the Invention

The present invention provides cells expressing a combination of an antigen-recognizing receptor that activates an immunoresponsive cell (e.g., TCR, CAR) and a chimeric co-stimulating receptor (CCR), and methods of using such cells for the treatment of a disease that requires an enhanced immune response. In one approach, tumor antigen-specific T cells, NK cells, CTL cells or other immunoresponsive cells are used as shuttles for the selective enrichment of one or more co-stimulatory ligands for the treatment or prevention of neoplasia. For example, a T cell expressing a chimeric antigen receptor 19z1 that recognizes CD19 is co-expressed in a T cell that expresses a chimeric co-stimulatory receptor P28BB that recognizes and binds Prostate Specific Membrane Antigen (PSMA). Such cells are administered to a human subject in need thereof for the treatment or prevention of prostate cancer. In another approach, viral antigen-specific T cells, NK cells, CTL cells can be used for the treatment of viral diseases. For example, a chimeric co-stimulatory antigen receptor that recognizes a first CMV antigen and a chimeric antigen receptor that recognizes and binds a second CMV antigen are co-expressed in cytotoxic T lymphocytes for the treatment of CMV.

Tumor Antigen-Specific T Lymphocytes (and NK Cells)

Types of tumor antigen-specific human lymphocytes that can be used in the methods of the invention include, without limitation, peripheral donor lymphocytes genetically modified to express chimeric antigen receptors (CARs) (Sadelain, M., et al. 2003 *Nat Rev Cancer* 3:35-45), peripheral donor lymphocytes genetically modified to express a full-length tumor antigen-recognizing T cell receptor complex comprising the a and p heterodimer (Morgan, R. A., et al. 2006 *Science* 314:126-129), lymphocyte cultures derived from tumor infiltrating lymphocytes (TILs) in tumor biopsies (Panelli, M. C., et al. 2000 *J Immunol* 164:495-504; Panelli, M. C., et al. 2000 *J Immunol* 164:4382-4392), and selectively in vitro-expanded antigen-specific peripheral bloodleukocytes employing artificial antigen-presenting cells (AAPCs) or pulsed dendritic cells (Dupont, J., et al. 2005 *Cancer Res* 65:5417-5427; Papanicolaou, G. A., et al. 2003 *Blood* 102:2498-2505). The T cells may be autologous, allogeneic, or derived in vitro from engineered progenitor or stem cells.

Any suitable tumor antigen (antigenic peptide) is suitable for use in the tumor-related embodiments described herein. Sources of antigen include, but are not limited to cancer proteins. The antigen can be expressed as a peptide or as an intact protein or portion thereof. The intact protein or a portion thereof can be native or mutagenized. Suitable antigens include prostate specific membrane antigen (PSMA) and prostate stem cell antigen (PCSA).

Viral Antigen-Specific T Lymphocytes (and NK Cells)

Suitable antigens for use in the treatment of pathogen infection or other infectious disease, for example, in an immunocompromised subject include, without limitation, viral antigens present in Cytomegalovirus (CMV), Epstein Barr Virus (EBV), Human Immunodeficiency Virus (HIV), and influenza virus.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

Accordingly, the invention generally provides an immunoresponsive cell, such as a virus specific or tumor specific T cell comprising a receptor that binds a first antigen and activates the immunresponsive cell and a receptor that binds a second antigen and stimulates the immunresponsive cell.

Vectors

Genetic modification of immunoresponsive cells (e.g., T cells, CTL cells, NK cells) can be accomplished by transducing a substantially homogeneous cell composition with a recombinant DNA construct. Preferably, a retroviral vector (either gamma-retroviral or lentiviral) is employed for the introduction of the DNA construct into the cell. For example, a polynucleotide encoding a receptor that binds an antigen (e.g., a tumor antigen, or a variant, or a fragment thereof), can be cloned into a retroviral vector and expression can be driven from its endogenous promoter, from the retroviral long terminal repeat, or from a promoter specific for a target cell type of interest. Non-viral vectors may be used as well.

For initial genetic modification of the cells to provide tumor or viral antigen-specific cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD 114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Other transducing viral vectors can be used to express a co-stimulatory ligand of the invention in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990).

Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1c enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can then be grown under conditions similar to those for unmodified cells, whereby the modified cells can be expanded and used for a variety of purposes.

Also included in the invention are 19z1, CD19, CD8, CD3, dsRed, P28BB, PSMA, CD28, 4-1BB, GFP polypeptides or fragments thereof that are modified in ways that enhance their anti-neoplastic activity when expressed in an immunoresponsive cell. The invention provides methods for optimizing an amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, 90%, 91%, 92%, 93%, 94%, 95%, 96%, 97%, 98%, 99% or more identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^3$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., —or -amino acids.

In addition to full-length polypeptides, the invention also provides fragments of any one of the polypeptides or peptide domains of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80, 100, 200, 300 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the invention. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. Preferably, the protein analogs are relatively resistant to in vivo degradation, resulting in a more prolonged therapeutic effect upon administration. Assays for measuring functional activity include, but are not limited to, those described in the Examples below.

Co-Stimulatory Ligands

The interaction with at least one co-stimulatory ligand provides a non-antigen specific signal important for full activation of an immune cell (e.g., T cell). Co-stimulatory ligands include, without limitation, tumor necrosis factor (TNF) ligands, cytokines (such as IL-2, IL-12, IL-15 or IL21), and immunoglobulin (Ig) superfamily ligands.

Tumor necrosis factor (TNF) is a cytokine involved in systemic inflammation and stimulates the acute phase reaction. Its primary role is in the regulation of immune cells. Tumor necrosis factor (TNF) ligands share a number of common features. The majority of the ligands are synthesized as type II transmembrane proteins (extracellular C-terminus) containing a short cytoplasmic segment and a relatively long extracellular region. TNF ligands include, without limitation, nerve growth factor (NGF), CD4OL (CD4OL)/CD154, CD137L/4-1BBL, tumor necrosis factor alpha (TNFa), CD134L/OX4OL/CD252, CD27L/CD70, Fas ligand (FasL), CD3OL/CD153, tumor necrosis factor beta (TNF(3)/lymphotoxin-alpha (LTa), lymphotoxin-beta (ur(3), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28.

Compositions comprising genetically modified immunoresponsive cells of the invention (e.g., T cells, NK cells, CTL cells, or their progenitors) can be provided systemically or directly to a subject for the treatment of a neoplasia, pathogen infection, or infectious disease. In one embodiment, cells of the invention are directly injected into an organ of interest (e.g., an organ affected by a neoplasia). Alternatively, compositions comprising genetically modified immunoresponsive cells are provided indirectly to the organ of interest, for example, by administration into the circulatory system (e.g., the tumor vasculature). Expansion and differentiation agents can be provided prior to, during or after administration of the cells to increase production of T cells, NK cells, or CTL cells in vitro or in vivo.

The modified cells can be administered in any physiologically acceptable vehicle, normally intravascularly, although they may also be introduced into bone or other convenient site where the cells may find an appropriate site for regeneration and differentiation (e.g., thymus). Usually, at least $1 \times 10^5$ cells will be administered, eventually reaching $1 \times 10^{10}$, or more. Genetically modified immunoresponsive cells of the invention can comprise a purified population of cells. Those skilled in the art can readily determine the percentage of genetically modified immunoresponsive cells in a population using various well-known methods, such as fluorescence activated cell sorting (FACS). Preferable ranges of purity in populations comprising genetically modified immunoresponsive cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Dosages can be readily adjusted by those skilled in the art (e.g., a decrease in purity may require an increase in dosage). The cells can be introduced by injection, catheter, or the like. If desired, factors can also be included, including, but not limited to, interleukins, e.g. IL-2, IL-3, IL-6, and IL-11, as well as the other interleukins, the colony stimulating factors, such as G-, M- and GM-CSF, interferons, e.g. .gamma.-interferon and erythropoietin.

Compositions of the invention include pharmaceutical compositions comprising genetically modified immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations

Compositions of the invention comprising genetically modified immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the genetically modified immunoresponsive cells as described in the present invention. This will present no problem to those skilled in chemical and pharmaceutical principles, or problems can be readily avoided by reference to standard texts or by simple experiments (not involving undue experimentation), from this disclosure and the documents cited herein. One consideration concerning the therapeutic use of genetically modified immunoresponsive cells of the invention is the quantity of cells necessary to achieve an optimal effect. The quantity of cells to be administered will vary for the subject being treated. In a one embodiment, between $10^4$ to $10^{10}$, between $10^5$ to $10^9$, or between $10^6$ and $10^8$ genetically modified immunoresponsive cells of the invention are administered to a human subject. More effective cells may be administered in even smaller numbers. In some embodiments, at least about $1\times10^8$, $2\times10^8$, $3\times10^8$, $4\times10^8$, and $5\times10^8$ genetically modified immunoresponsive cells of the invention are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Methods of Treatment

Provided herein are methods for treating neoplasia in a subject. Also contemplated herein are methods for treating a pathogen infection or other infectious disease in a subject, such as an immunocompromised human subject. The methods comprise administering a T cell, NK cell, or CTL cell of the invention in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the antigen-binding fragment administered.

For adoptive immunotherapy using antigen-specific T cells, cell doses in the range of $10^6$-$10^{10}$ (e.g., $10^9$) are typically infused. Upon administration of the genetically modified cells into the host and subsequent differentiation, T cells are induced that are specifically directed against the specific antigen. "Induction" of T cells can include inactivation of antigen-specific T cells such as by deletion or anergy. Inactivation is particularly useful to establish or reestablish tolerance such as in autoimmune disorders. The modified cells can be administered by any method known in the art including, but not limited to, intravenous, subcutaneous, intranodal, intratumoral, intrathecal, intrapleural, intraperitoneal and directly to the thymus.

The invention provides methods for increasing an immune response in a subject in need thereof. In one embodiment, the invention provides methods for treating or preventing a neoplasia in a subject. The invention provides therapies that are particularly useful for the treatment of subjects having prostate cancer, or metastatic prostate cancer that is not amenable to conventional therapeutic interventions. Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in this invention is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

Human neoplasia subjects having any of the following neoplasias: glioblastoma, melanoma, neuroblastoma, adenocarcinoma, glioma, soft tissue sarcoma, and various carcinomas (including prostate and small cell lung cancer) are especially appropriate subjects. Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Accordingly, the invention provides a method of treating or preventing a neoplasia in a subject, the method comprising administering an effective amount of an immunoresponsive cell comprising a receptor that binds a tumor antigen and activates the immunoresponsive cell (e.g., TCR, CAR) and a vector encoding a receptor that binds another tumor antigen and stimulates the immunoresponsive cell. In one embodiment, the neoplasia is selected from the group consisting of prostate cancer, breast cancer, blood cancers (e.g. leukemias, lymphomas, and myelomas), ovarian cancer, bladder cancer, brain cancer, colon cancer, intestinal cancer, liver cancer, lung cancer, pancreatic cancer, prostate cancer, skin cancer, stomach cancer, glioblastoma, and throat cancer. In another embodiment, the tumor antigen is one or more of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD133, CD138, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Ra2), is-light chain, kinase insert domain receptor (KDR), Lewis Y (LeY), LI cell adhesion molecule (LlCAM), melanoma antigen family A, 1 (MAGE-A1), Mucin 1 (MUC1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), or Wilms tumor protein (WT-1).

As a consequence of surface expression of a receptor that binds a tumor antigen and activates the immunoresponsive cell (e.g., TCR, CAR) and a vector encoding a receptor that binds another tumor antigen and stimulates the immunoresponsive cell (e.g. CCR), adoptively transferred human T or NK cells are endowed with augmented and selective cytolytic activity at the tumor site. Furthermore, subsequent to their localization to tumor or viral infection and their proliferation, co-stimulatory ligand expressing T cells turn the tumor or viral infection site into a highly conductive environment for a wide range of immune cells involved in the physiological anti-tumor or antiviral response (tumor infiltrating lymphocytes, NK-, NKT-cells, dendritic cells, and macrophages).

In other embodiments, the invention provides methods for treating subjects with a pathogen infection (e.g., viral infection, bacterial infection, fungal infection, parasite infection, or protozoal infection). The invention is particularly useful for enhancing an immune response in an immunocompromised subject. Exemplary viral infections susceptible to treatment using a method of the invention include, but are not limited to, Cytomegalovirus (CMV), Epstein Barr Virus (EBV), Human Immunodeficiency Virus (HIV), and influenza virus infections.

Accordingly, the invention provides a method of treating or preventing a pathogen infection in a subject, the method comprising administering an effective amount of an immunoresponsive cell as described herein.

Kits

The invention provides kits for the treatment or prevention of a neoplasia, pathogen infection, immune disorder or allogeneic transplant. In one embodiment, the kit includes a therapeutic or prophylactic composition containing an effective amount of an immunoresponsive cell comprising an activating antigen receptor and a co-stimulatory antigen receptor in unit dosage form. In particular embodiments, the cells further comprise a co-stimulatory ligand. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired the immunoresponsive cell is provided together with instructions for administering the cell to a subject having or at risk of developing a neoplasia, pathogen infection, immune disorder or allogeneic transplant. The instructions will generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening,

Example 1. T Cells Co-Expressing a Chimeric Antigen Receptor (CAR) and a Chimeric Co-Stimulating Receptor (CCR) Eradicated Established Tumors The invention provides "tumor-sensing T cells" that simultaneously engage two antigens co-expressed by a tumor cell. Importantly, it has been found that the reactivity against tissues expressing either antigen alone should be negligible, only unleashing T cell activation in the presence of both antigens but not either one alone. The invention is at least based in part on the discoveries that in combination provide selective T cell immunoreactivity, and, thus, make this approach clinically relevant. The first is to assign T cell activation to one antigen (e.g., CD19 or prostate stem cell antigen, PSCA), which may be mediated by a T cell receptor (TCR) or a chimeric antigen receptor (CAR). Costimulation is independently mediated by a "chimeric costimulatory receptor" (CCR),[12, 13] which is targeted to a second antigen (e.g., prostate-specific membrane antigen, PSMA). This approach resulted in increased immunoreactivity against dual antigen positive (DP) tumors, but failed to avert enhanced immunoreactivity against single antigen positive (SP) tumors. The second principle important for tumor sensing T cells to differentiate DP tumors from SP tumors, is to diminish T cell activation to a level where it is by itself ineffective, but functionally rescued at the tumor site by a CCR engaged by an independent, co-expressed antigen. As CARs and CCRs recognize cell surface antigens rather than HLA-peptide complexes, T cells engineered in this manner are directly targeted to the tumor and will not be costimulated by interacting with cells cross-presenting the targeted antigens. As demonstrated herein, this approach resulted in selective tumor eradication in multiple tumor-bearing mice.

Figure 1B:
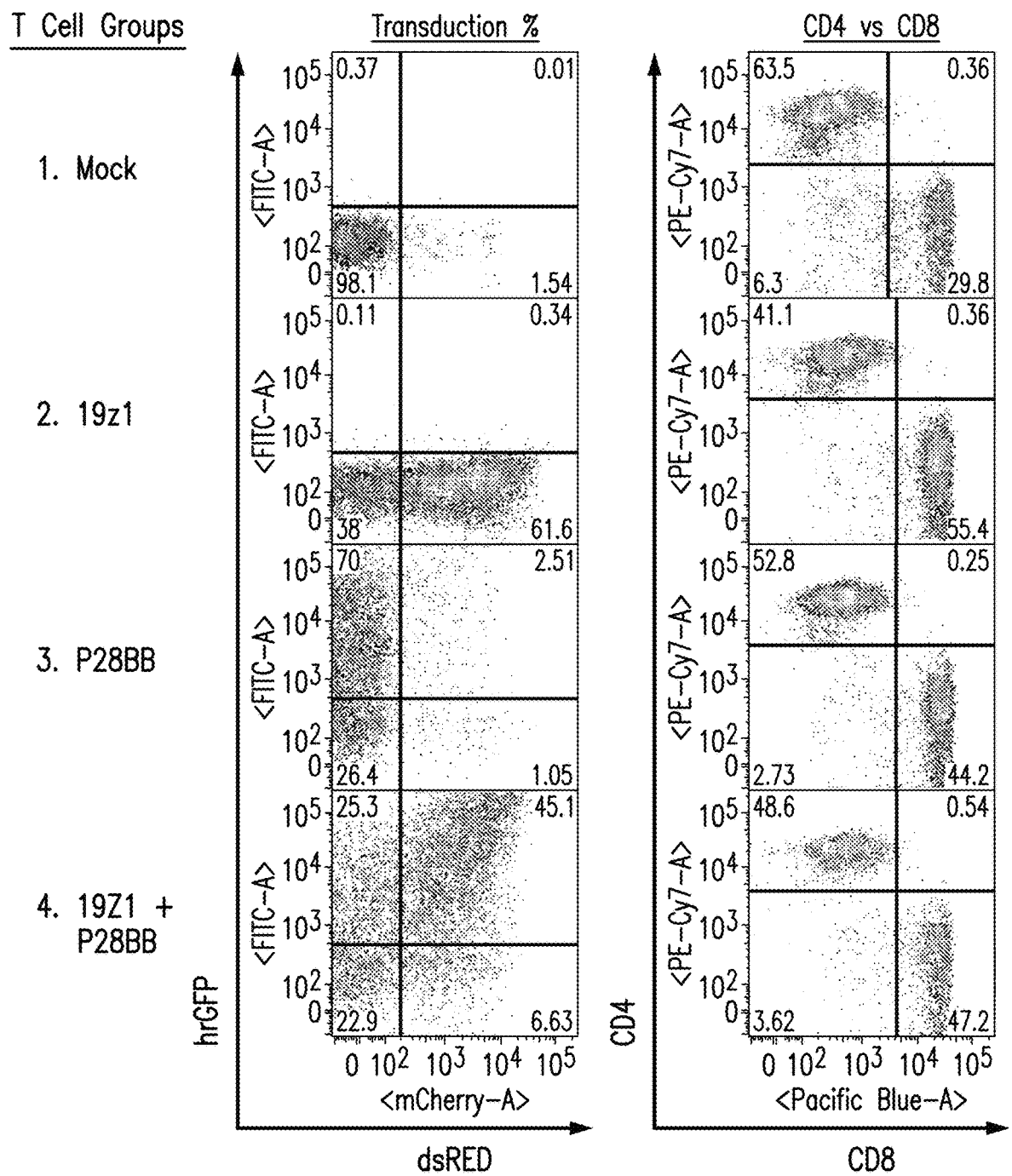

To demonstrate that both T cell activation and costimulation signals can be supplied in vivo using two distinct antigen-specific receptors, the combination of a CAR, providing a CD3 activation signal upon recognition of the B cell marker CD19[14] and a CCR specific for PSMA[12, 15] was evaluated. Because of the synergy between CD28 and 4-1BB[16, 17] including tandem cytoplasmic domains[18-21], 4-1BB cytoplasmic domain was added to the PSMA CCR P28[15] as described[2] (FIG. 1A). Primary human peripheral blood T cells were transduced with the 19z1 and/or P28BB receptors and showed readily detectable expression of both receptors, with transduction efficiencies in the range of 4570% (FIG. 1B). Four groups of T cells were analyzed in all subsequent studies, comprising anti-CD19 CAR (19z1), anti-PSMA CCR (P28BB), both anti-CD19 CAR and anti-PSMA CCR in combination (19z1+P28BB), and a mock-transduced control group (mock) (FIG. 1C). The in vitro cytotoxic and proliferative response upon exposure to CD19 and/or PSMA showed that cytotoxicity directed against CD19 was, as expected, imparted by 19z1 and unaltered in the presence of PSMA.

Figure 4C:
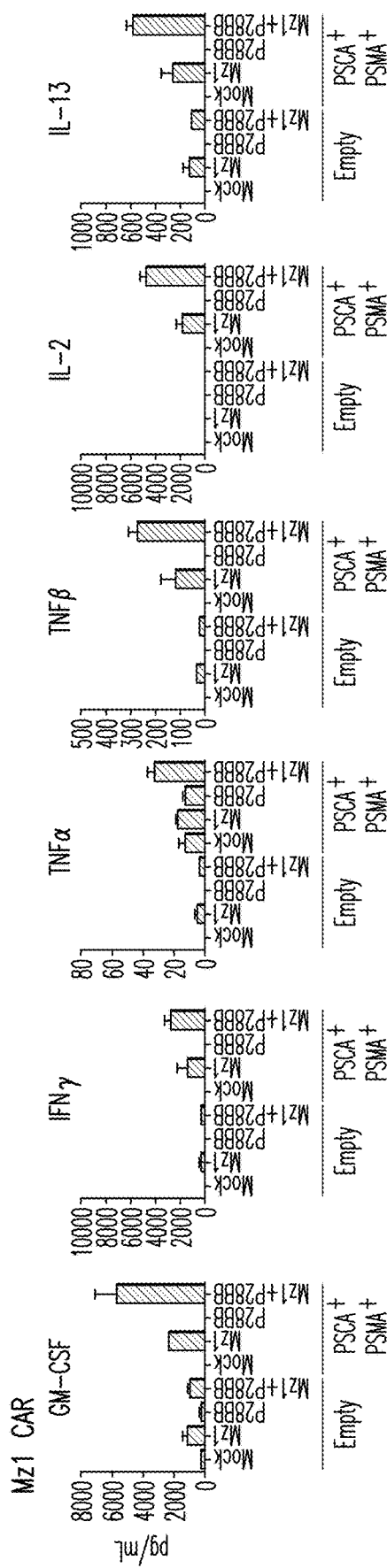
Figure 4D:
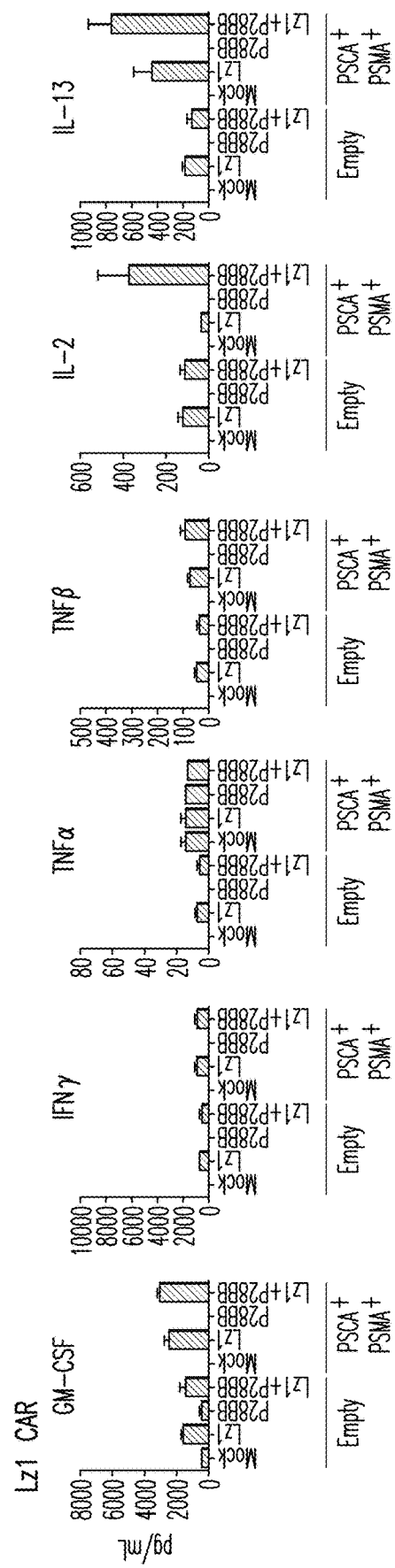
Figure 4E:
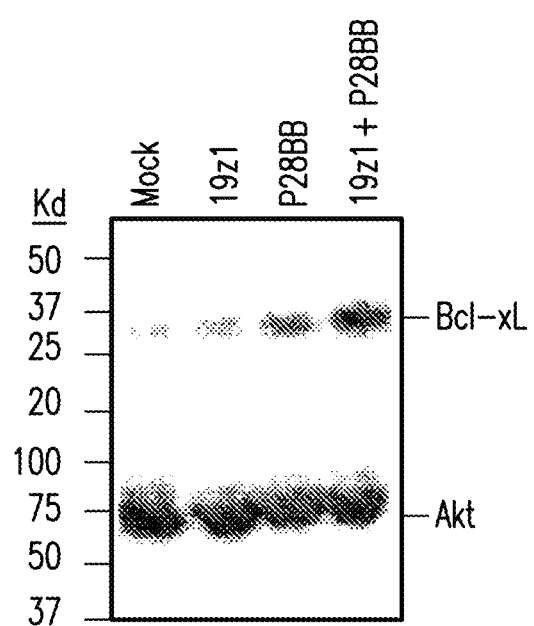
FIG. 4E depicts Western blot analysis for BclxL performed using cellular lysates of untransduced T cells or T cells transduced with 19z1, P28BB, or both after 24 hours post initial antigen stimulation. Total amount of Akt was used as a loading control.

A quantitative comparison of the T cell groups, normalized to the fraction of 19z1-transduced T cells for the 19z1 and 19z1+P28BB groups and the P28BB-transduced fraction in the P28BB group showed that 19z1 and 19z1+P28BB T cells specifically lysed 40-47% CD19$^+$ targets at the 50:1 E:T ratio while the P28BB-transduced T cells failed to lyse PSMA$^+$ targets (FIG. 2A). However, upon repeated exposure to these antigens in the absence of exogenous cytokine, only the 19z1+P28BB T cells exhibited robust proliferation with a 58-fold expansion for 31 days when co-cultured on artificial antigen presenting cells (AAPCs) that expressed both antigens. By comparison, 19z1 or P28BB T cells only displayed modest expansion over the first 14 days, as did the 19z1+P28BB T cells on CD19+PSMA APCs (FIG. 2B). Further evidence of stronger T cell activation in the presence of both antigens was provided by the quantitative assessment of cytokine production and the induction of the antiapoptotic molecule BclxL in 19z1+P28BB T cells, which were distinctly greater in the presence of CD19$^+$PSMA$^+$ APCs than in the presence of either antigen alone (FIGS. 4A, 4E).

Figure 2C:
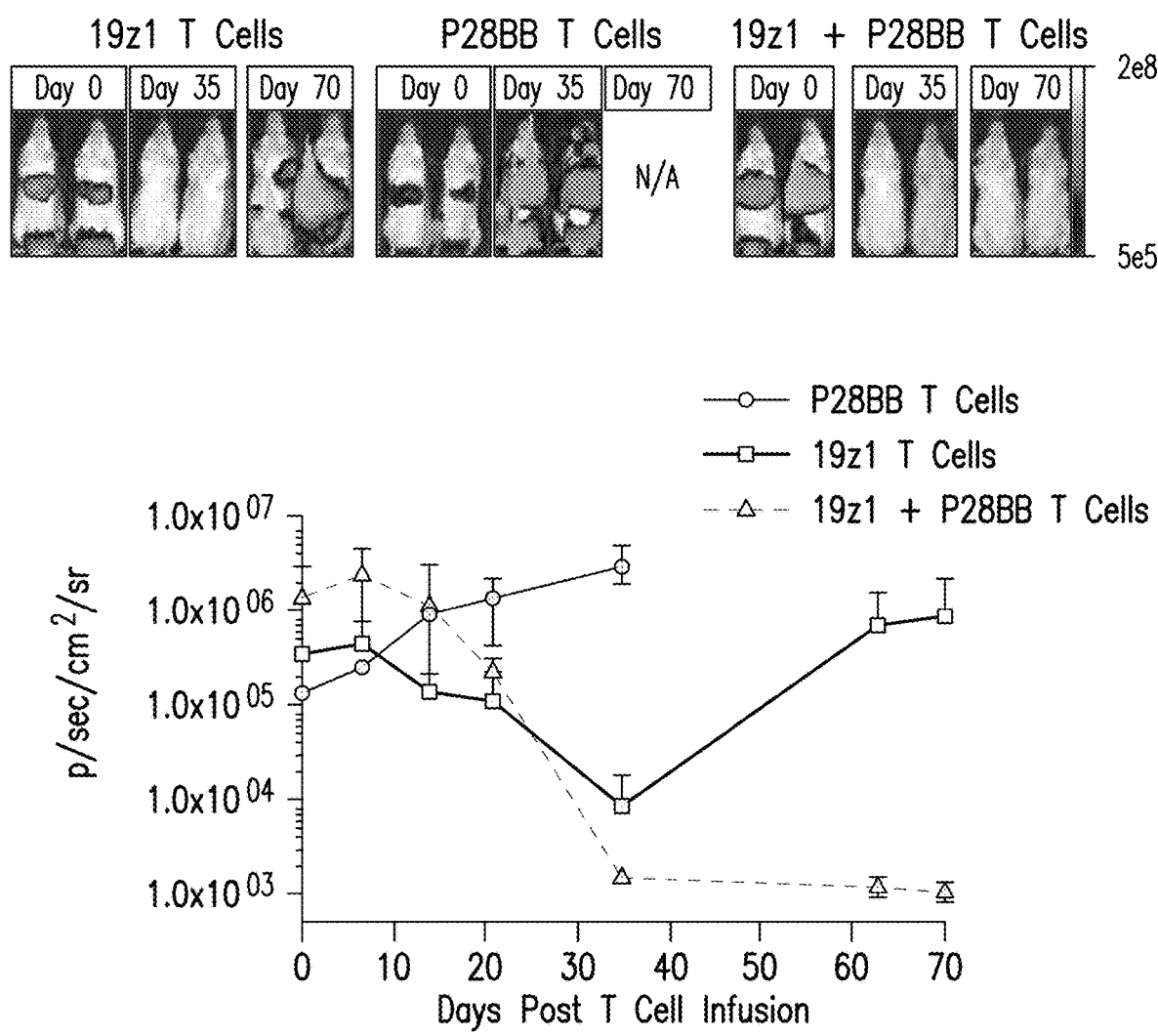

Initially, the in vivo ability of these dual-receptor expressing T cells to eradicate established systemic human prostate tumors in immunocompromised NOD/SCID-yC KO (NSG) mice bearing dual-positive (CD19+PSMA+) tumor cells was tested. The NSG mice were systemically engrafted with $2.0 \times 10^6$ firefly-luciferase expressing PC3 tumor cells that expressed both CD19 and PSMA (FIG. 5) and treated 19 days later with a single intravenous infusion of $1.0 \times 10^6$ 19z1, 19z1+P28BB, P28BB or control T cells. Thirty-five days later, mice that received P28BB T cells or control T cells were sacrificed due to tumor burden. In contrast, mice treated with 19z1 T cells had a marked reduction of tumor burden. Strikingly, mice treated with 19z1+P28BB T cells had undetectable tumor burden (FIG. 2C). Over 70 days of post-infusion monitoring, the CD19$^+$ tumors eventually relapsed in mice that received 19z1 T cells, while complete remission persisted in all mice that received 19z1+P28BB T cells (FIG. 2C). This result strongly indicated that tumor eradication had been achieved.

Figure 2D:
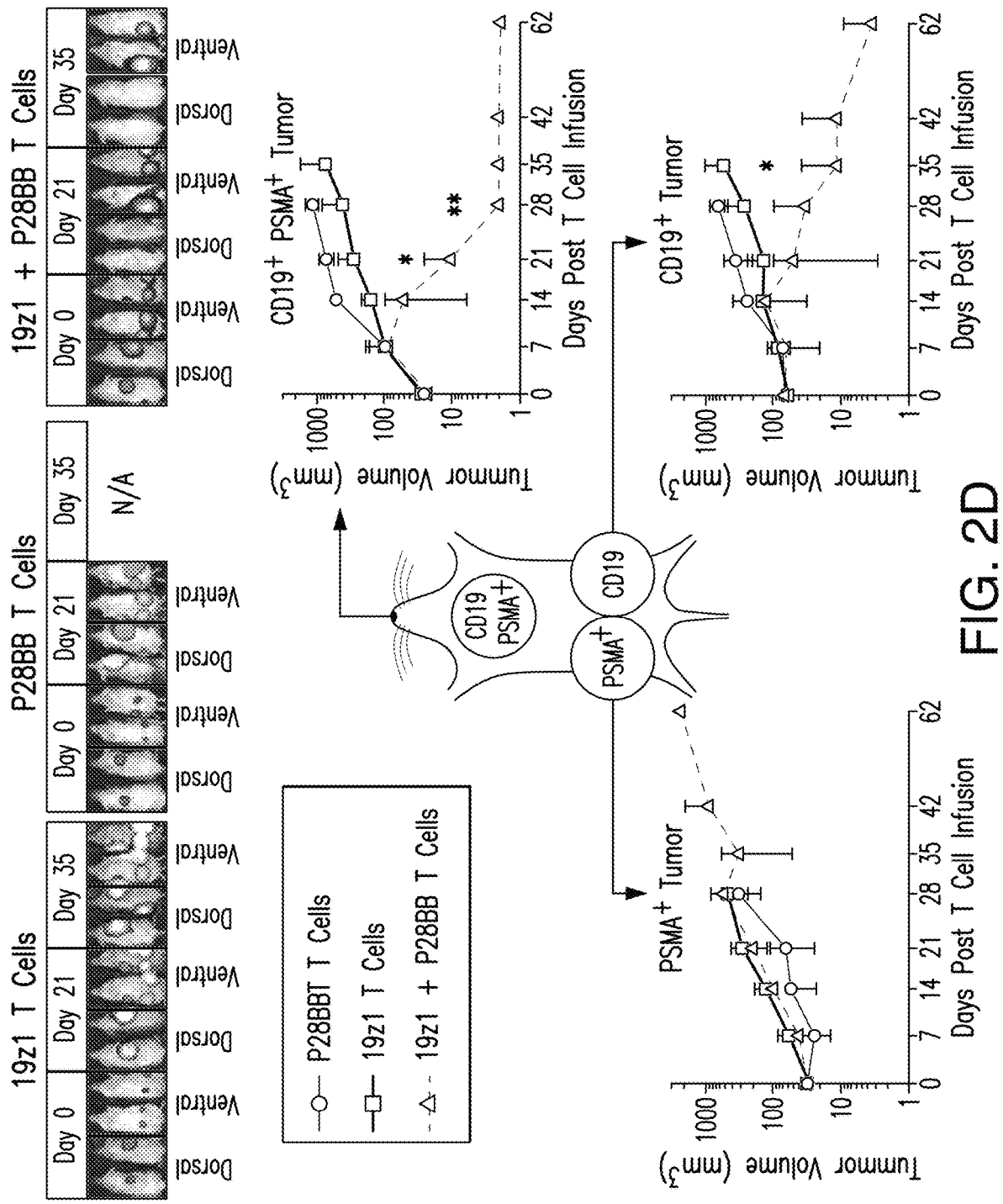

These findings however posed a concern because of the potential base line eradication of CD19$^+$PSMA tumors by 19z1+P28BB T cells. There was a likelihood that T cell immunoreactivity would be undesirably enhanced in recipients bearing dual-positive CD19$^+$PSMA$^+$ tumors due to recirculation of T cells. To test this hypothesis, mice were subcutaneously infused with CD19$^+$PSMA$^-$ tumors into the left flanks, CD19$^-$PSMA$^+$ tumors into the right flanks, and CD19$^+$PSMA$^+$ tumors into their backs. One week later, mice were administered one of 19z1, P28BB, or 19z1+P28BB T cells ($1.0 \times 10^6$ cells) intravenously. Mice that received P28BB T cells had progression of all three tumors and needed to be sacrificed within 35 days (FIG. 2D). In mice treated with 19z1 T cells, the CD19$^+$PSMA$^-$ and CD19$^+$PSMA$^+$ tumors underwent a substantial reduction compared to their progression in recipients of P28BB T cells, before eventually progressing. Consistent with prior results, mice treated with 19z1+P28BB T cells showed complete eradication of CD19+PSMA$^+$ tumors. However, as hypothesized, rejection of CD19$^+$PSMA$^-$ tumors was also substantially enhanced and superior to that observed in recipients of 19z1 T cells (FIG. 2D, lower panels). Thus, a split signal approach targeting two antigens failed to restrict T cell reactivity and to protect single antigen tumors.

Figure 3A:
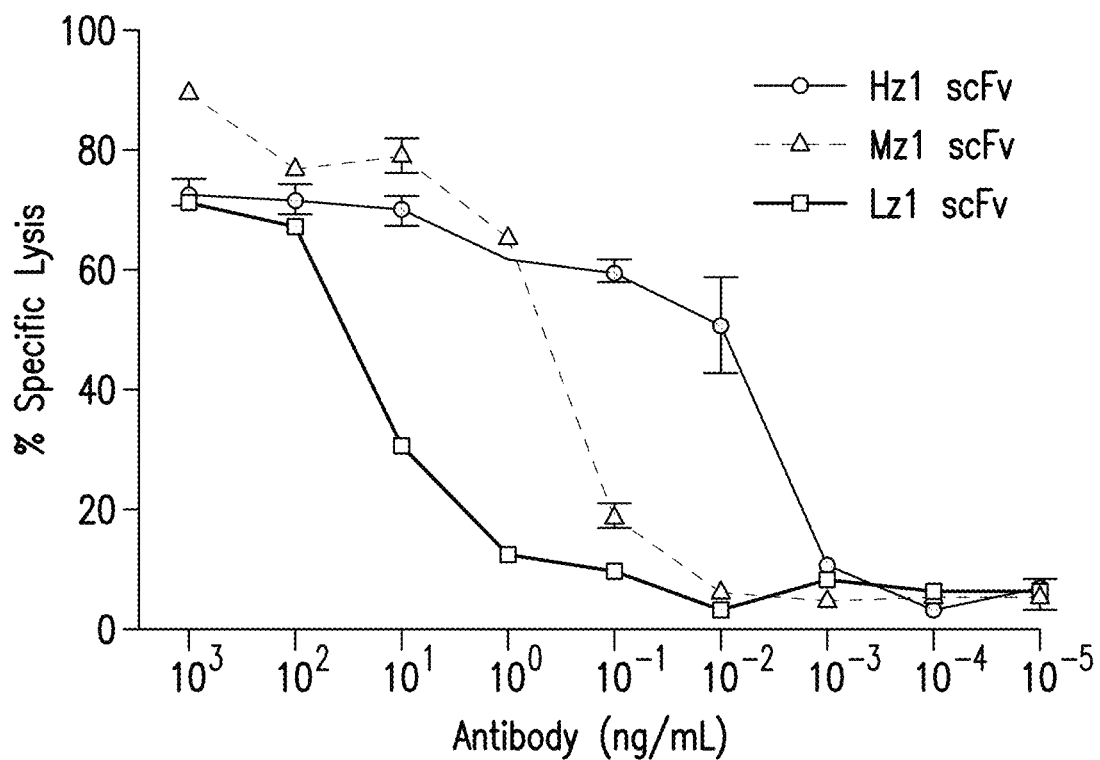
FIGS. 3A-3E depict that tumor-sensing $T_{(TTS)}$ cells selectively eradicated human prostate tumors when targeting two prostate tumor antigens.
Figure 3B:
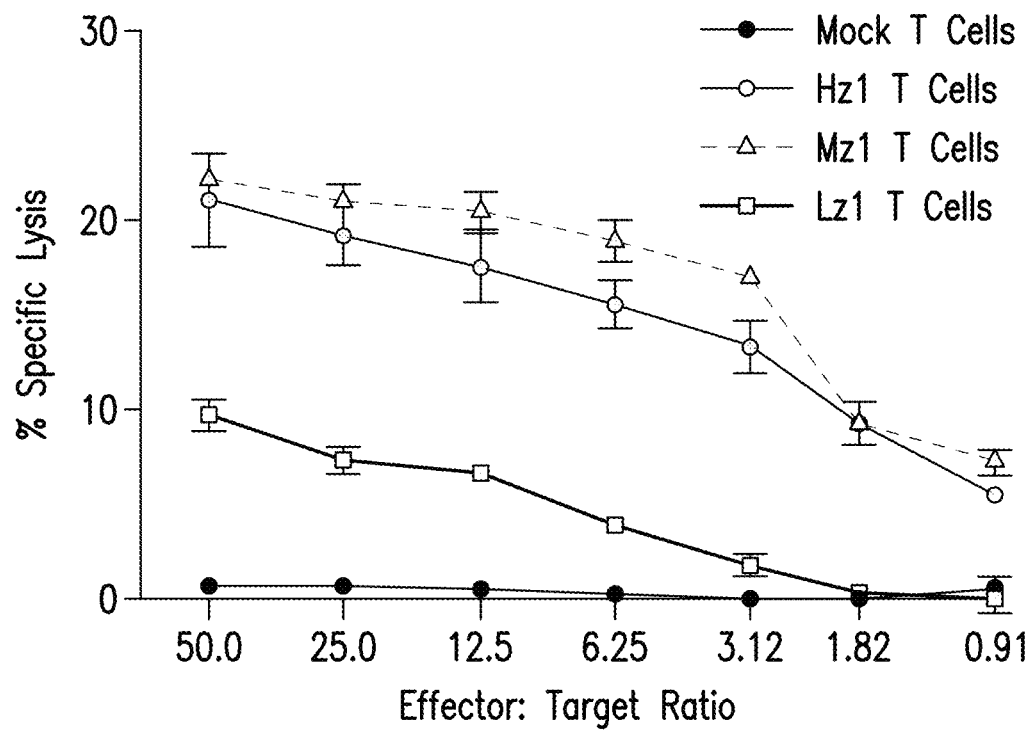

To address the problem of single antigen reactivity, it was proposed that T cell activation would have to be minimized, almost to the point of extinction, only to be rescued at the site of dual antigen expressing by an adequate CCR engagement. Thus, CARs with diminished activity were sought. For these experiments, a clinically relevant combination of antigens targeting PSCA and PSMA were used. Three PSCA-specific scFvs were evaluated with different binding affinities for PSCA (FIG. 3A). While the Hzl scFv efficiently lysed tumor cells down to the picogram range, the Lzl scFv required 1,000-10,000 fold more antibody to achieve similar efficiency of specific lysis. These scFvs were used to derive three CD3-based CARs with different activities in cytotoxicity assays (FIG. 3B). Two of the CARs, Hzl and Mzl, directed moderate lytic activity against PSCA+ targets (20% specific lysis at the 50:1 E:T ratio). In contrast the third CAR, Lzl, only reached 10%, qualifying it as a inefficient antigen receptor. This hierarchy was further confirmed in cytokine release assays, which showed enhanced cytokine secretion by 19z1+P28BB T cells (FIG. 4A) and Hzl+P28BB T cells (FIG. 4B) compared to cells with either receptor alone. This enhancement was less in Mzl+P28BB T cells (FIG. 4C) and even further decreased in Lzl+P28BB T cells (FIG. 4D).

Figure 3C:
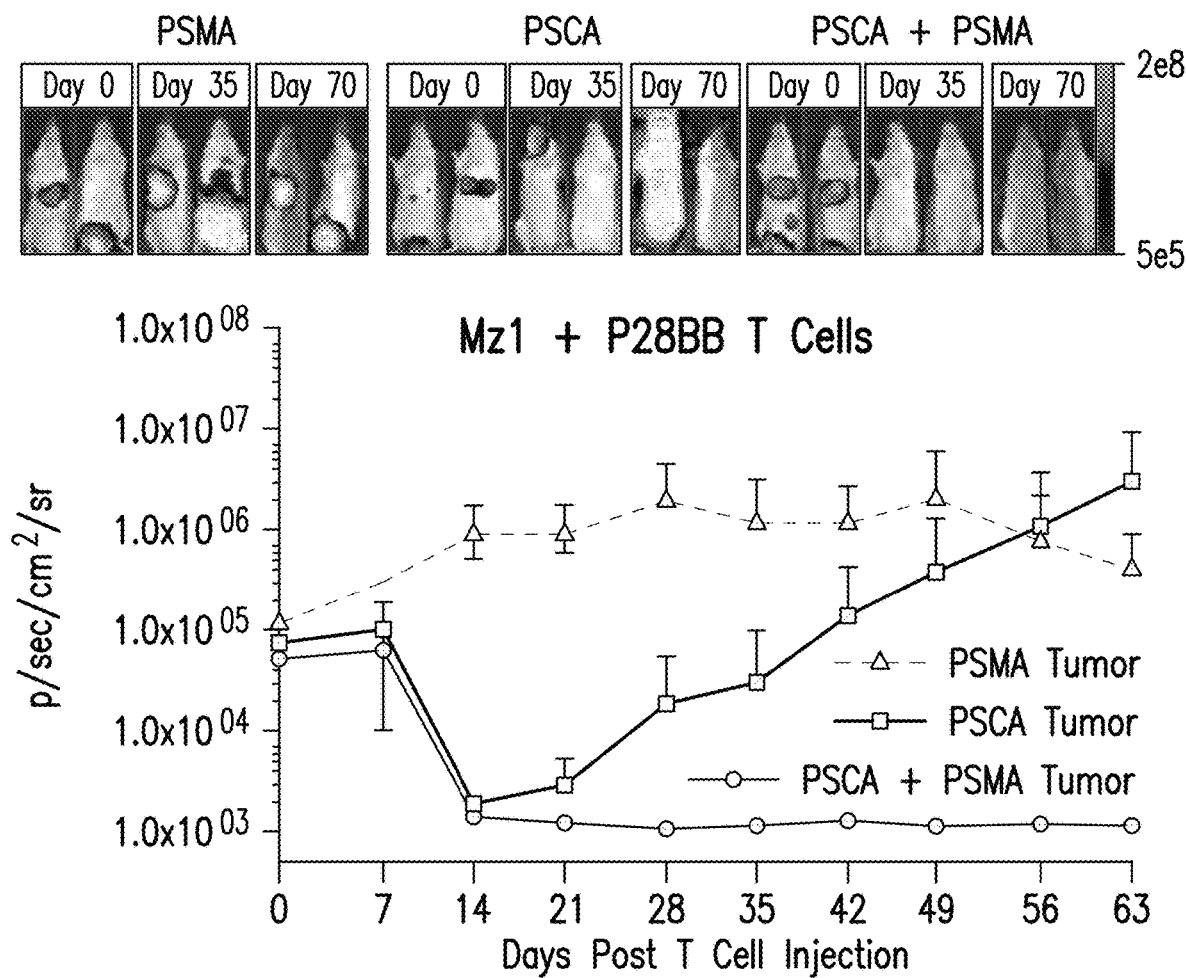
Figure 3D:
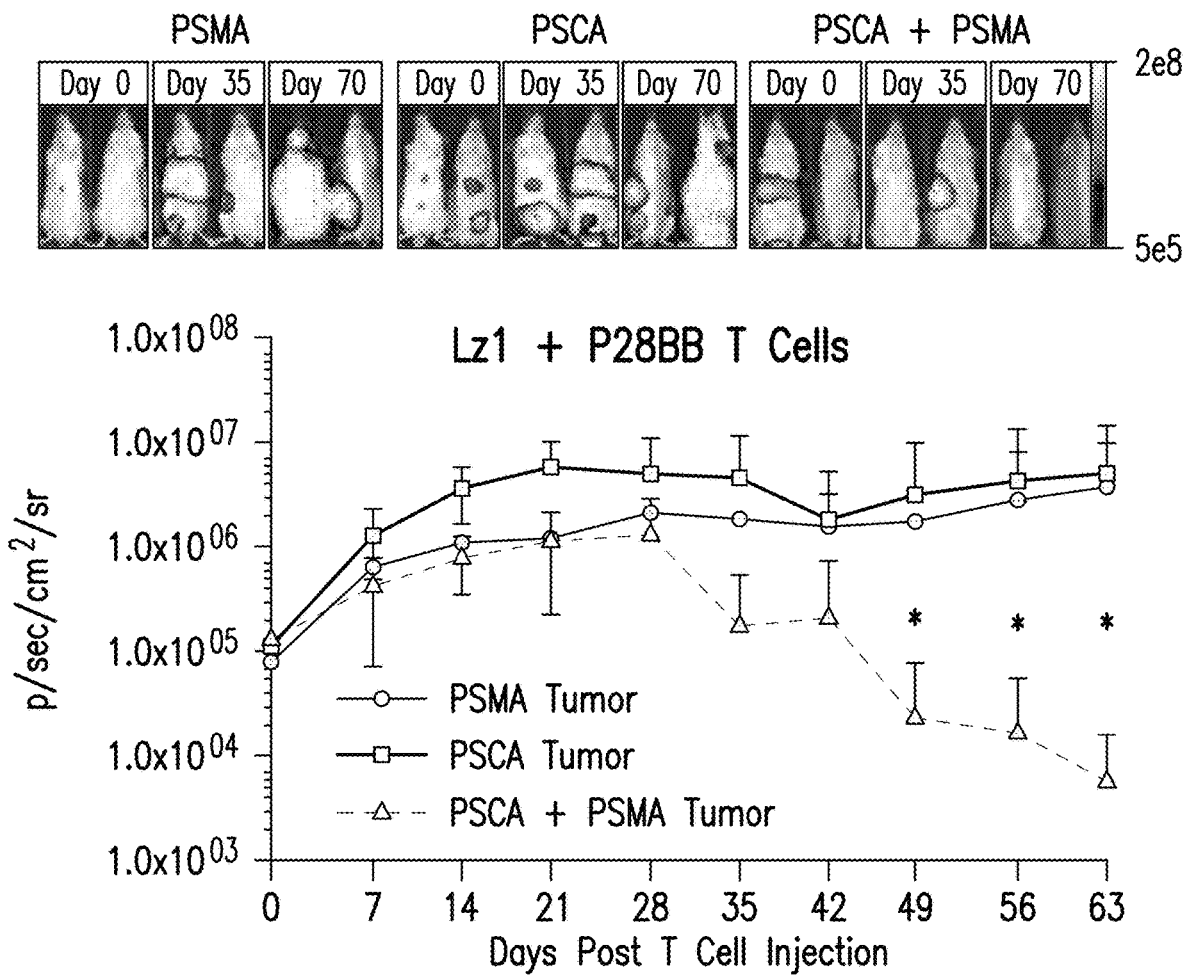
Figure 5:
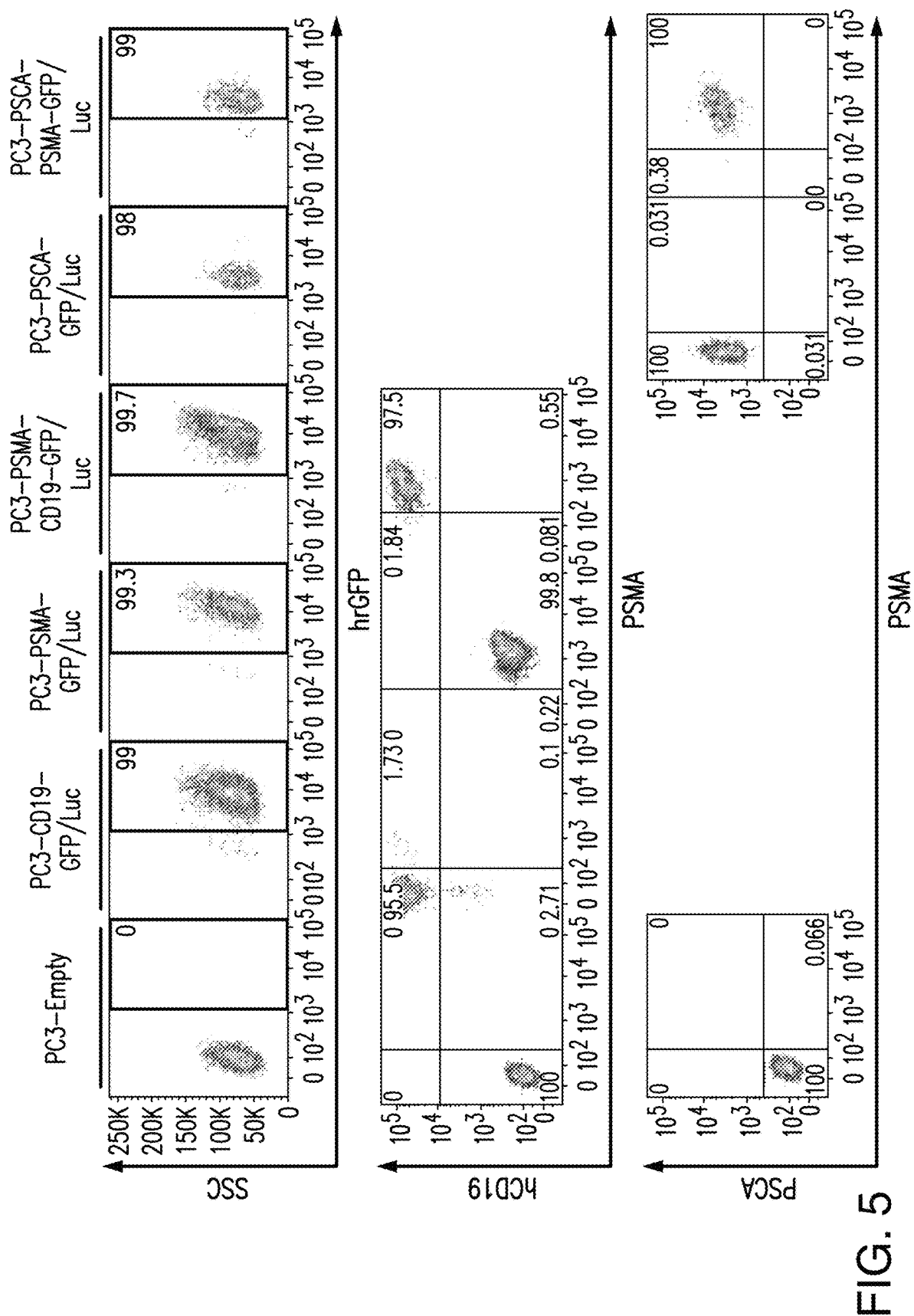
FIG. 5 depicts generation of prostate tumor cells for the expression of fusion protein GFP-Firefly Luciferase (GFP/Luc) and tumor antigens. Untransduced PC3 cells (Empty) were transduced with GFP/Luc and either CD19, PSMA, PSCA, or a combination of two antigens using retroviral expression constructs. Cells were purified via double purity FACS for GFP/Luc, CD19, PSMA, and/or PSCA.

In order to evaluate the therapeutic efficacy and targeting profile of PSCA+PSMA-reactive T cells, the anti-tumor activity of these T cells was tested in animals bearing PSCA+PSMA− and/or PSCA+PSMA+ tumors. First, to test the ability of Mzl+P28BB and Lzl+P28BB T cells to eradicate PSCA+PSMA+ cells selectively, mice were inoculated intravenously with 2×106 FFLuc-expressing PC3 cells positive for PSMA, PSCA, or both (FIG. 5). Fourteen days later, one set of mice received 1×106 Mzl+P28BB CAR+ T cells infused intravenously, and another set of received 1×106 Lzl+P28BB CARP T cells. Mice bearing PSCA+PSMA tumor cells that were treated with the more efficient Mzl+P28BB T cells exhibited greater tumor regression than mice treated with Lzl+PBB T cells (FIG. 3C). Similar to the CD19 experiment (FIG. 2C), these tumors eventually relapsed and progressed. However, in mice bearing PSCA+PSMA+ tumor cells Mzl+P28BB T cells induced robust and long-term tumor eradication. Consistent with the lesser potency of Lzl+P28BB T cells, tumor eradication in mice bearing PSCA+PSMA+ tumor cells treated with Lzl+P28BB T cells was slower but nonetheless equally successful, resulting in strong tumor eradication and long-term survival of all treated mice (FIG. 3C). Tumor eradication was not enhanced in control mice bearing either PSCAVPSMA− or PSCA−PSMA+ tumors (FIG. 3C). A more stringent evaluation of background activity against PSCAVSMA− tumors was tested in the context of animals also bearing PSCA+PSMA+ and PSCAPSMA+ tumors. Lzl+P28BB T cells mediated eradication of PSCA+PSMA+ tumors without increasing eradication of PSCA+PSMA tumors (FIG. 3E), which was not different from that induced by Lzl T cells.

Thus, these results demonstrate the feasibility of decreasing T cell activation to the point of averting immune reactivity against tissues expressing one targeted antigen and rescuing T cell activation at the tumor site where two antigens are co-expressed, without running the risk of igniting reactivity against the single antigen-expressing tissues. In doing so, the results demonstrate proof-of-principle for achieving two complementary outcomes that determine specificity and safety: 1) the ability to create targeting specificity in the absence of a unique target antigen through combinatorial antigen recognition; and 2) the protection of cells expressing only one of the antigens by titrating activation and costimulatory signals, so as to practically confine activation to sites of target antigen coexpression.

Figure 6A:
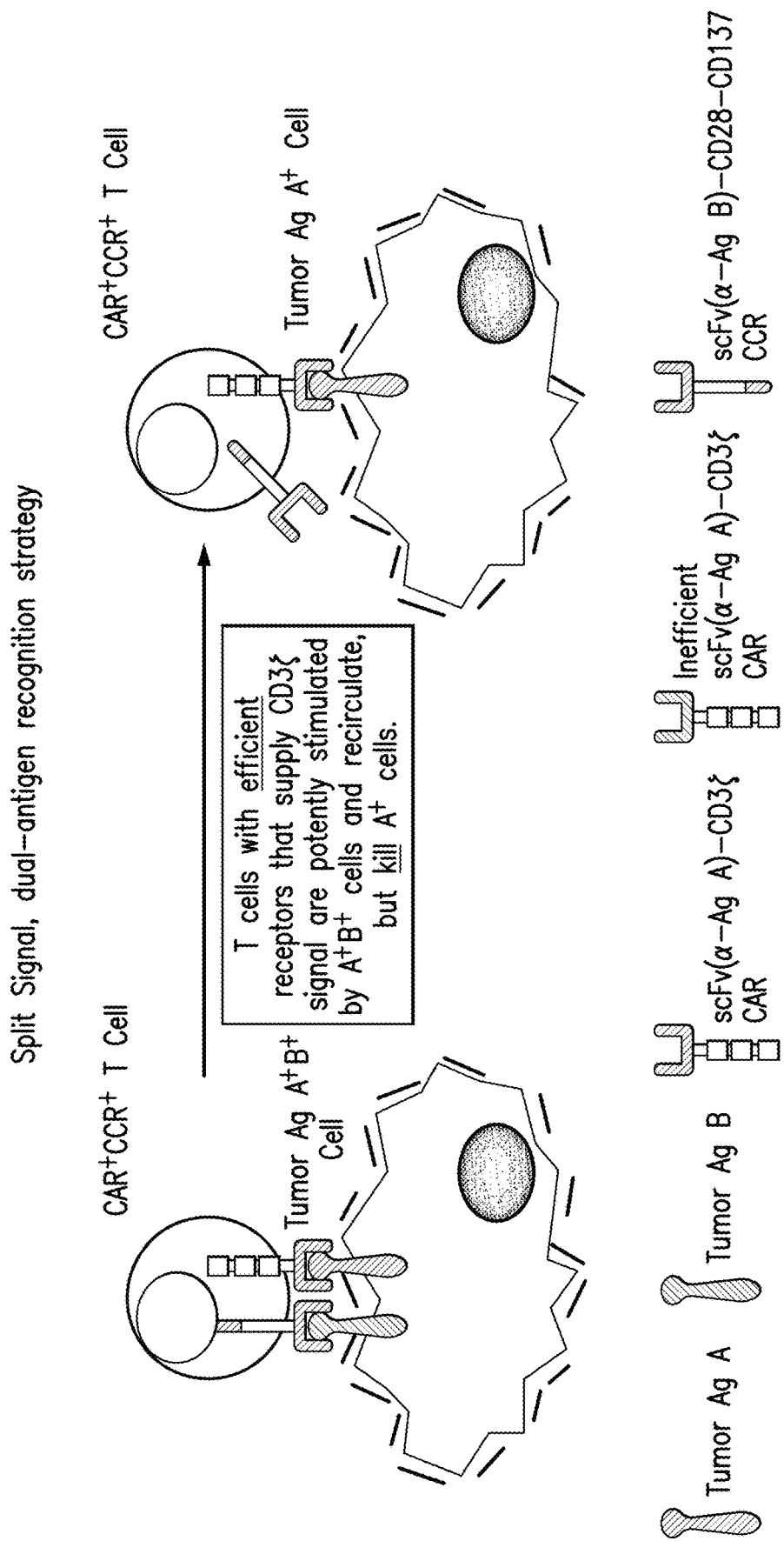
FIGS. 6A-6C illustrate the tumor-sensing T cell concept.
Figure 6B:
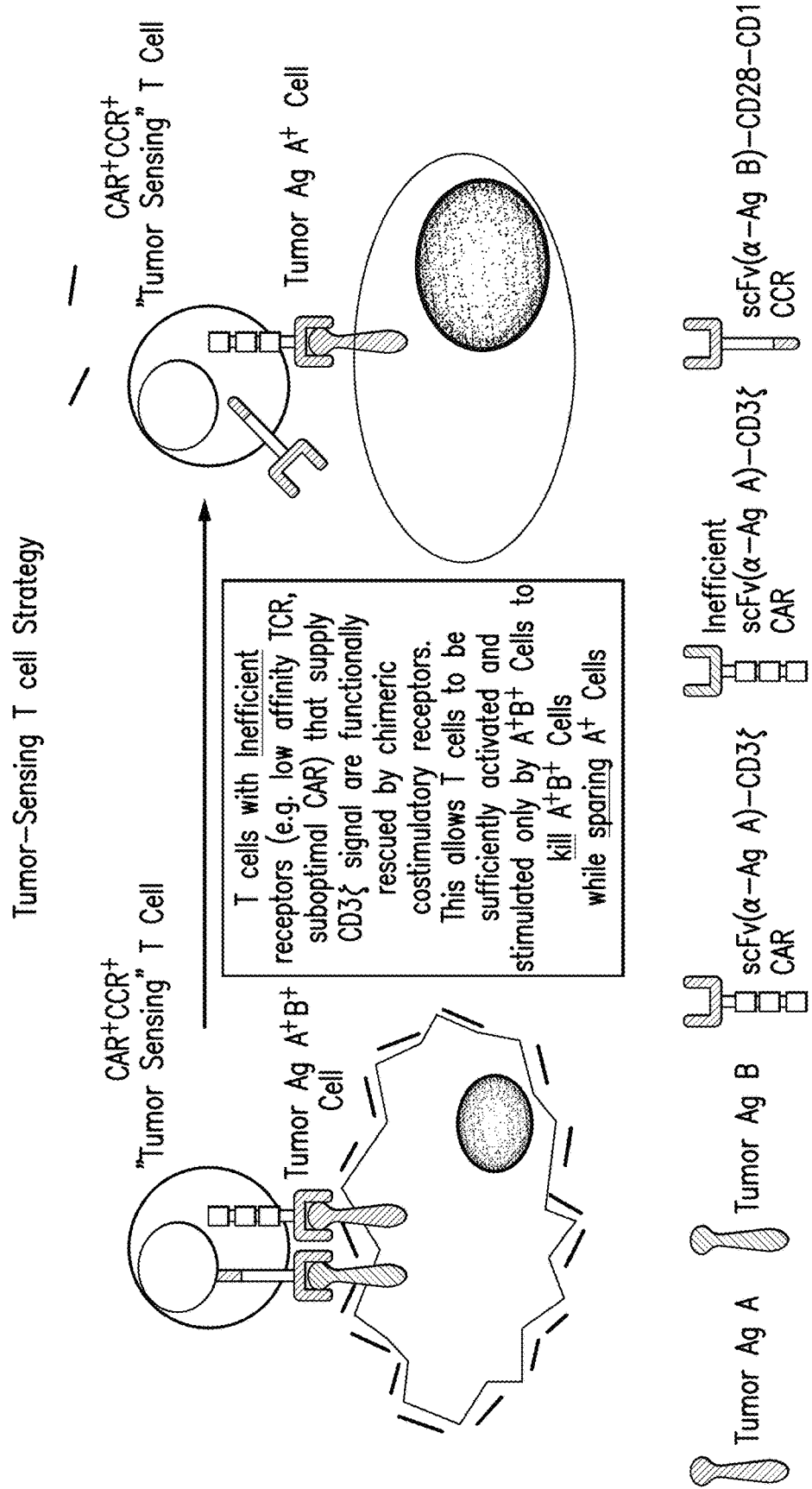
Figure 6C:
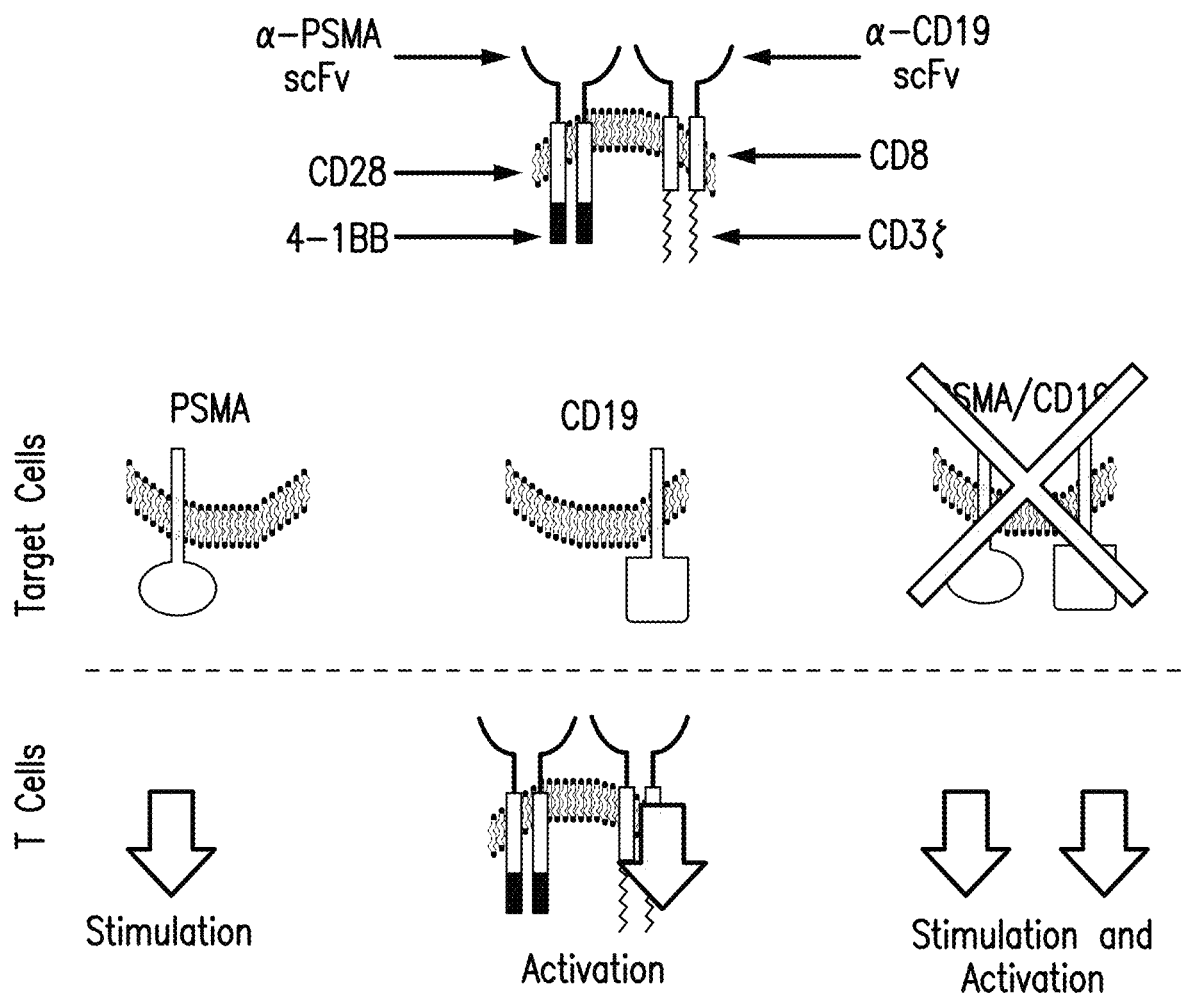

Targeted T cell therapies have the potential to provide curative treatments but their applicability is limited by the paucity of validated tumor-specific targets. Extra-tumoral expression results indeed in "on-target, off-tumor" effects that 2-4[11] may be sometimes tolerable but are eventually lethal[11]. The method described herein provides improved targeting by supplying titrated activation and costimulation signals through combinatorial antigen recognition (FIGS. 6A-6C).

Figure 3E:
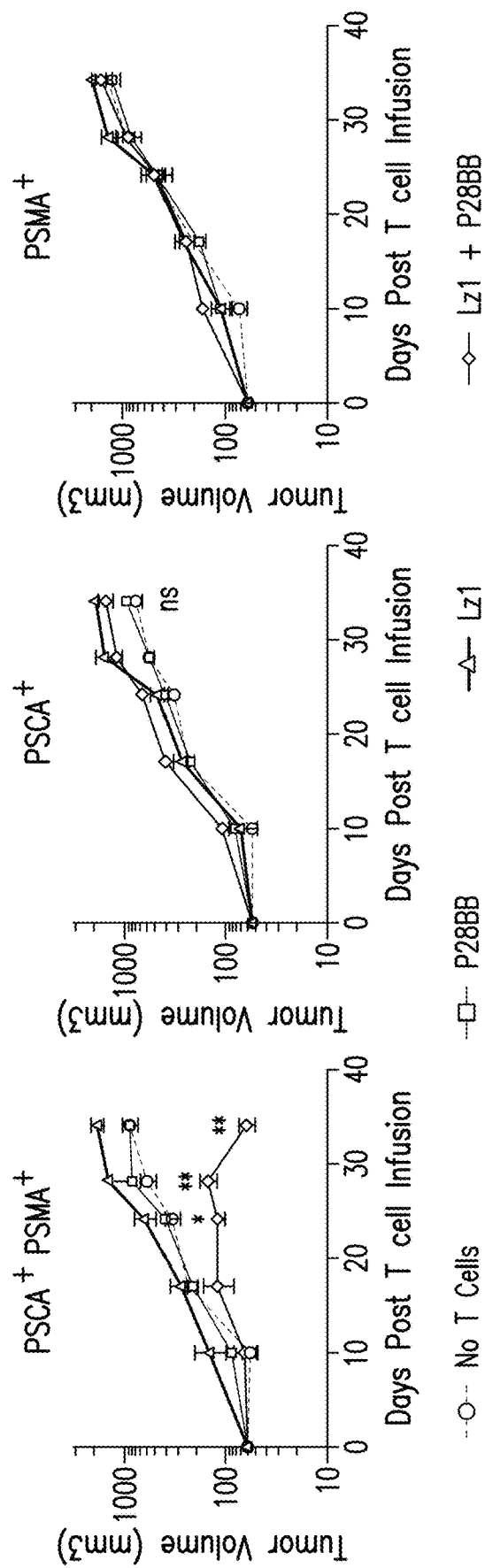

In physiological antigen presentation,[22] T cells are primed in lymph nodes by receiving activating and costimulatory signals and migrate to peripheral sites, where effector functions of the T cells are not as dependent on costimulation. Similarly, T cells engaged through an antigen receptor and a CCR may recirculate to other peripheral sites and display heightened cytolytic activity against tissues expressing only one of the targeted antigens (FIG. 6A). Therefore, the present strategy was developed to address this problem of a potential systemic effect in order to spare cells singly positive for the antigen, including non-tumor cells (FIG. 6B). In a tri-tumor mouse model (PSCA+, PSMA+, and PSCA+PSMA+), eradication of PSCAVSMA+ was accomplished, while sparing the PSCA+PSMA− and PSCA−PSMA+ tumors (FIG. 3E).

As shown by the present studies, this selectivity for DP tumors can be achieved by reducing the efficacy of the CAR, which creates cells that are less cytotoxic (FIG. 3B) and that have reduced levels of cytokine secretion (FIGS. 4A-4D). While the levels of both TH 1 and TH2 cytokines are relatively high for both 19z1 and Hzl CARs, using less efficient CARs Mzl and Lzl resulted in reducing these levels. The enhancement of cytokine levels in LzI+P28BB T cells compared to Lzl T cells was minimal except for IL-2 and IL-13. While IL-2 induces proliferation and can promote either a TH 1 or TH2 response[23], IL-13 is associated with a TH2 response specific to 4-IBB/CD137 signaling.[24,25]

PSCA and PSMA are promising targets for the treatment of metastatic prostate cancer[26,27], although neither is absolutely prostate-specific. In human subjects, PSCA expression is found in prostate cancer and within the renal pelvis, ureter, urinary bladder, and urethra.[28] Expression of PSMA strongly correlates with primary prostate cancer, metastases, as well as in astrocytes type II, the kidney proximal tubule and the intestinal brush border.[29] Dual PSCA/PSMA targeting is thus expected to increase prostate cancer targeting and reduce reactivity against these normal tissues. It is appreciated that this principle can be extended to other tumor types which express a pair of antigens, especially those that confer true tumor-specificity. For example, HER2, MUC1, CD44, CD49f, and/or EpCAM could be used in this manner to treat breast cancer.[31] Likewise, mesothelin, folate receptor-a, CD44, and/or CD133 could be used to treat ovarian cancer.[32, 33] The targeting of tumor initiating cells or cancer stem cells, for which unique target antigens/structures have not yet been clearly identified[34, 35] would be particularly attractive using this approach.

An important aspect of this approach is to constrain and nearly abolish T cell activation in response to a single antigen. CARs with low affinity or low avidity that only provide a poor activation signal were found to be useful for achieving this effect. Alternatively, an endogenous TCR with low affinity or low avidity may be used in combination with a CCR to provide antigen-specific costimulation. Altogether, the results indicate the advantages of restricting the activity of engineered T cells, reconciling potency with safety through combinatorial antigen recognition by tumor-sensing T cells.

Gammaretroviral Vector Construction and Viral Production

The gammaretroviral vector SFG-19z1 has been extensively described.[14] This backbone construct was used to exchange scFvs to generate SFG-Hzl, SFG-Mzl, and SFG-Lzl by directional cloning utilizing a NcoI site located 5' of the scFv and a NodI site located 3' of the scFv. To generate SFG-P28BB, the fused CD28 and CD137 domains were PCR amplified from SFG-P28BBz1 and ligated 3' of the PSMA scFv using a 5' NcoI site and a 3' BamHI site to include a stop codon 3' of the BB domain, while the CD3 domain was removed.[21] Bicistronic gene expression for CARs to be coexpressed with dsRED and CCRs to be coexpressed with hrGFP was achieved by using an Internal Ribosomal Entry Site as previously described. Vectors were used to transiently transfect cell lines to generate stable viral producing lines as previously described.

Generation of Anti-PSCA scFvs

Three novel PSCA specific scFvs, termed Hz1, Mz1, and Lz1 were generated by amplifying the variable heavy (VH) and variable light (VL) domains conferring PSCA antigen specificity of non-overlapping epitopes using degenerate primers from hybridomas as previously described.[36] These VH and $V_L$ domains were fused together using a linker and were used to replace the CD19 scFv in the SFG-19z1 backbone using 5'Sphl to 3'Notl sites.

Isolation, Retroviral Transduction, and Culture of Primary Human T Cells

Peripheral blood leukocytes were isolated using Ficoll gradients and transduced as previously described. Briefly, after 48-hour activation with 2 &g/mL phytohemagglutinin, cells were transduced twice via spinoculation for 1 hour on retronectin coated plates over the next 48 hours and 20 U/mL of TL-2 was added. After allowing 3 days for vector expression, transduction efficiencies were determined via flow cytometry and bulk unsorted cells were used for various assays or adoptive transfers.

Generation of Antigen Expressing Tumor Cell Lines

The PC3 human prostate tumor line was obtained from ATCC and retrovirally[16] transduced in order to generate PC3-GFP/Luc, which was subsequently used to create 10 PC3-CD19, PC3-PSMA, PC3-CD19-PSMA, PC3-PSCA, and PC3-PSCA-PSMA via retroviral transduction.

CTL Chromium Release Killing Assays

Target cells expressing desired antigen were labeled with $^{51}$Cr and co-cultured with T cells at decreasing effector. target ratio's. After 4 hours of culture, supernatant was removed and used to measure radioactivity released from chromium. Specific lysis was determined by subtracting background radioactivity of target cells not cultured with T cells and dividing by the radioactivity measured from target cells completely lysed by using 0.2% Triton X-100.

Long-Term T Cell Proliferation Assays

Tumor cells expressing desired antigen were irradiated with 30 Gy prior to co-culture with $1.0 \times 10^6$ T cells at a 5:1 effector: target ratio. T cells were counted weekly using an Invitrogen Countess cell counter and then re-stimulated with irradiated tumor cells. No exogenous cytokines were added to these co-cultures.

Generation of Tumor Models in Mice

PC3 tumor cells were infused into NOD/SCID-IL2Ry mice obtained from either Jackson Laboratories or from in-house breeding under the protocol 04-10-024 approved by the MSKCC Institutional Animal Care and Use Committee. For systemic tumor experiments, $2.0 \times 10^6$ tumor infused into mice with $1.0 \times 10^6$ chimeric receptor positive T cells infused 14 days later. For subcutaneous tumor experiments, $1.0 \times 10^6$ tumor cells were injected per tumor site, established for 7 days upon which $1.0 \times 10^6$ chimeric positive T cells were infused IV.

Quantification of Tumor Burden

For systemic tumor experiments, bioilluminescent imaging (BLI) was used to quantitatively measure tumor burden by correlating the amount of tumor burden to luminescence by using an IVIS 100 system (Caliper Life Sciences) as previously described. For subcutaneous tumors, calipers were used to measure tumor size. Tumor volume was calculated by multiplying the length, width, and height of each tumor.

Bispecific Antibody Mediated Tumor Lysis

Bispecific antibodies containing a PSCA specific scFv fused to a CD3 specific scFv were added at various amounts to untransduced T cells co-cultured with PSCA$^+$PC3 at a 20:1 ratio, respectively in standard 4 hr chromium release assay assays.

Flow Cytometry

Cells were analyzed using an LSRII flow cytometer or sorted using a FACSAria cell sorter (BD Biosciences) as previously described.[16] Detection of chimeric receptor at the cell surface could be achieved directly by using AF647 conjugated goat-anti-mouse antibody (Invitrogen). Antibodies for CD4-PE-Cy7, CD8-Pacific Blue, and CD19-APC were obtained from Invitrogen while PSCA antibodies were purified from hybridoma supernatants and PSMA antibodies were obtained from MBL International.

Cytokine Analysis

Supernatants harvested 48 hours after the second tumor stimulation from long-term T cell proliferation experiments and were used for cytokine analysis by using a custom multiplex system HCYTMAG-60K (Millipore) and analyzed using a Luminex 100 instrument (Luminex) as previously described.[21]

Western Blot Analysis

Cells were harvested 24 hours after initial tumor stimulation from long-term T cell proliferation experiments to be used for western blot analysis of Bcl$_x$L expression. Western blots were performed as previously described[21] using Bcl$_x$L and Akt primary antibodies (Cell Signaling Technology).

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to U.S. patent application Ser. No. 12/593,751, which is the U.S. national phase application, pursuant to 35 U.S.C. § 371, of International Patent Application No.: PCT/US2008/004251, filed Mar. 8, 2010, which claims the benefit of U.S. Provisional Application Ser. No. 60/921,144, filed Mar. 30, 2007, the disclosures of which are hereby incorporated herein in their entireties by reference.

REFERENCES

1. Robbins, P. F. et al. Tumor regression in patients with metastatic synovial cell sarcoma and melanoma using genetically engineered lymphocytes reactive with NY-ESO-1. Journal of clinical oncology: official journal of the American Society of Clinical Oncology 29, 917-924 (2011).
2. Kalos, M. et al. T cells with chimeric antigen receptors have potent antitumor effects and can establish memory in patients with advanced leukemia. Sci Transl Med 3, 95ra73 (2011).
3. Brentjens, R. J. et al. Safety and persistence of adoptively transferred autologous CD19-targeted T cells in patients with relapsed or chemotherapy refractory B-cell leukemias. Blood 118, 4817-4828 (2011).

4. Kochenderfer, J. N. et al. B-cell depletion and remissions of malignancy along with cytokine-associated toxicity in a clinical trial of anti-CD19 chimeric-antigen-receptor-transduced T cells. Blood 119, 2709-2720 (2012).
5. Sadelain, M., Riviere, I. & Brentjens, R. Targeting tumours with genetically enhanced T lymphocytes. Nat Rev Cancer 3, 35-45 (2003).
6. Ho, W. Y., Blattman, J. N., Dossett, M. L., Yee, C. & Greenberg, P. D. Adoptive immunotherapy: engineering T cell responses as biologic weapons for tumor mass destruction. Cancer cell 3, 431-437 (2003).
7. Rosenberg, S. A., Restifo, N. P., Yang, J. C., Morgan, R. A. & Dudley, M. E. Adoptive cell transfer: a clinical path to effective cancer immunotherapy. Nature reviews. Cancer 8, 299-308 (2008).
8. Sadelain, M., Brentjens, R. & Riviere, I. The promise and potential pitfalls of chimeric antigen receptors. Curr Opin Immunol 21, 215-223 (2009).
9. Jorritsma, A., Schotte, R., Coccoris, M., de Witte, M. A. & Schumacher, T. N. Prospects and limitations of T cell receptor gene therapy. Current gene therapy 11, 276-287 (2011).
10. Johnson, L. A. et al. Gene therapy with human and mouse T, cell receptors mediates cancer regression and targets normal tissues expressing cognate antigen. Blood 114, 535-546 (2009).
11. Morgan, R. A. et al. Case report of a serious adverse event following the administration of T cells transduced with a chimeric antigen receptor recognizing ERBB2. Molecular therapy: the journal of the American Society of Gene Therapy 18, 843-851 (2010).
12. Krause, A. et al. Antigen-dependent CD28 signaling selectively enhances survival and proliferation in genetically modified activated human primary T lymphocytes. J Exp Med 188, 619-626 (1998).
13. Wilkie, S. et al. Dual Targeting of ErbB2 and MUC1 in Breast Cancer Using Chimeric Antigen Receptors Engineered to Provide Complementary Signaling. Journal of clinical immunology (2012).
14. Brentjens, R. J. et al. Eradication of systemic B-cell tumors by genetically targeted human T lymphocytes co-stimulated by CD80 and interleukin-15. Nature medicine 9, 279-286 (2003).
15. Maher, J., Brentjens, R. J., Gunset, G., Riviere, I. & Sadelain, M. Human T-lymphocyte cytotoxicity and proliferation directed by a single chimeric TCRzeta/CD28 receptor. Nat Bio technol. 20, 70-75 (2002).
16. Stephan, M. T. et al. T cell-encoded CD80 and 4-1BBL induce auto- and transcostimulation, resulting in potent tumor rejection. Nature medicine 13, 1440-1449 (2007).
17. Watts, T. H. TNF/TNFR family members in costimulation of T cell responses. Annual review of immunology 23, 23-68 (2005).
18. Wang, J. et al. Optimizing adoptive polyclonal T cell immunotherapy of lymphomas, using a chimeric T cell receptor possessing CD28 and CD137 costimulatory domains. Human gene therapy 18, 712-725 (2007).
19. Carpenito, C. et al. Control of large, established tumor xenografts with genetically retargeted human T cells containing CD28 and CD137 domains. Proceedings of the National Academy of Sciences of the United States of America 106, 3360-3365 (2009).
20. Tammana, S. et al. 4-1BB and CD28 signaling plays a synergistic role in redirecting umbilical cord blood T cells against B-cell malignancies. Hum Gene Ther 21, 75-86 (2010).
21. Zhong, X. S., Matsushita, M., Plotkin, J., Riviere, I. & Sadelain, M. Chimeric antigen receptors combining 4-1BB and CD28 signaling domains augment PI3kinase/AKT/Bcl-XL activation and CD8+ T cell-mediated tumor eradication. Molecular therapy: the journal of the American Society of Gene Therapy 18, 413-420 (2010).
22. Schwartz, R. H. T cell energy. Annual review of immunology 21, 305-334 (2003).
23. Liao, W., Lin, J. X. & Leonard, W. J. IL-2 family cytokines: new insights into the complex roles of IL-2 as a broad regulator of T helper cell differentiation. Current opinion in immunology 23, 598-604 (2011).
24. Nam, K. O., Shin, S. M. & Lee, H. W. Cross-linking of 4-IBB up-regulates IL-13 expression in CD8(+) T lymphocytes. Cytokine 33, 87-94 (2006).
25. Shin, S. M. et al. 4-IBB triggers IL-13 production from T cells to limit the polarized, Th1-mediated inflammation. Journal of leukocyte biology 81, 1455-1465 (2007).
26. Saeki, N., Gu, J., Yoshida, T. & Wu, X. Prostate stem cell antigen: a Jekyll and Hyde molecule? Clinical cancer research: an official journal of the American Association for Cancer Research 16, 3533-3538 (2010).
27. Olson, W. C., Heston, W. D. & Rajasekaran, A. K. Clinical trials of cancer therapies targeting prostate-specific membrane antigen. Reviews on recent clinical trials 2, 182-190 30 (2007).
28. Lam, J. S. et al. Prostate stem cell antigen is overexpressed in prostate cancer metastases. Clinical cancer research: an official journal of the American Association for Cancer Research 11, 2591-2596 (2005).
29. Silver, D. A., Pellicer, I., Fair, W. R., Heston, W. D. & Cordon-Cardo, C. Prostate-specific membrane antigen expression in normal and malignant human tissues. Clinical cancer research: an official journal of the American Association for Cancer Research 3, 81-85 (1997).
30. Liu, J. C. et al. Seventeen-gene signature from enriched Her2/Neu mammary tumor-initiating cells predicts clinical outcome for human HER2+:ERalpha-breast cancer. Proceedings of the National Academy of Sciences of the United States of America 109, 58325837 (2012).
31. Meyer, M. J. et al. CD44posCD49fhiCD133/2hi defines xenograft-initiating cells in estrogen receptor-negative breast cancer. Cancer research 70, 4624-4633 (2010).
32. Strauss, R. et al. Analysis of epithelial and mesenchymal markers in ovarian cancer reveals phenotypic heterogeneity and plasticity. PloS one 6, el 6186 (2011).
33. Shihle, M. & Davidson, B. Pathogenesis of ovarian cancer: clues from selected overexpressed genes. Future Oncol 5, 1641-1657 (2009).
34. Nguyen, L. V., Vanner, R., Dirks, P. & Eaves, C. J. Cancer stem cells: an evolving concept. Nature reviews. Cancer 12, 133-143 (2012).
35. Magee, J. A., Piskounova, E. & Morrison, S. J. Cancer stem cells: impact, heterogeneity, and uncertainty. Cancer cell 21, 283-296 (2012).
36. Orlandi, R., Gussow, D. H., Jones, P. T. & Winter, G. Cloning immunoglobulin variable domains for expression by the polymerase chain reaction. Proceedings of the National Academy of Sciences of the United States of America 86, 3833-3837 (1989).

What is claimed is:

1. A method of producing an immunoresponsive cell or a pharmaceutical composition comprising the immunoresponsive cell, the method comprising introducing into the immunoresponsive cell:

a first nucleic acid molecule encoding a chimeric antigen receptor (CAR) that binds to a first antigen with a dissociation constant (Kd) of about $5 \times 10^{-8}$ M or more, wherein binding of the CAR to the first antigen is capable of delivering an activation signal to the immunoresponsive cell, and a second nucleic acid molecule encoding a chimeric co-stimulating receptor (CCR) that binds to a second antigen, wherein binding of the CCR to the second antigen is capable of delivering a costimulatory signal to the immunoresponsive cell but does not alone deliver an activation signal to the immunoresponsive cell;

wherein the immunoresponsive cell is capable of i) exhibiting negligible cytolytic activity against cells that are singly positive for the first antigen, and ii) inducing cytolytic activity against cells that are positive for both the first and second antigens.

2. The method of claim 1, wherein the first antigen is a tumor antigen or a pathogen antigen.

3. The method of claim 1, wherein the first and second antigens are independently selected from the group consisting of:

a) CAIX, CEA, CD5, CD7, CD10, CD19, CD20, CD22, CD30, CD33, CD34, CD38, CD41, CD44, CD49f, CD56, CD74, CD133, CD138, a cytomegalovirus (CMV) infected cell antigen, EGP-2, EGP-40, EpCAM, Erb-B2, Erb-B3, Erb-B4, FBP, Fetal acetylcholine receptor, folate receptor-a, GD2, GD3, HER-2, hTERT, IL-13R-a2, K-light chain, KDR, LeY, LI cell adhesion molecule, MAGE-AI, MUC1, Mesothelin, NKG2D ligands, NY-ESO-1, oncofetal antigen (h5T4), PSCA, PSMA, ROR1, TAG-72, VEGF-R2, and WT-1;

b) CD133, a cytomegalovirus (CMV) infected cell antigen, Erb-B2, KDR, Mesothelin, NKG2D ligands, NY-ESO-1, oncofetal antigen (h5T4), PSCA, PSMA, CD19, VEGF-R2, and WT-1; or c) HER2, MUC1, CD44, CD49f, EpCAM, CEA, CD133, a cytomegalovirus (CMV) infected cell antigen, EGP-2, EGP-40, Erb-B2, Erb-B3, Erb-B4, FBP, KDR, Mesothelin, NKG2D ligands, NY-ESO-1, oncofetal antigen (h5T4), PSCA, PSMA, VEGF-R2, and WT-1.

4. The method of claim 1, wherein the tumor and/or neoplasm is breast cancer, and the first and second tumor antigens are distinct antigens independently selected from the group consisting of HER2, MUC1, CD44, CD49f, EpCAM, CEA, CD133, a cytomegalovirus (CMV) infected cell antigen, EGP-2, EGP-40, Erb-B2, Erb-B3, Erb-B4, FBP, KDR, Mesothelin, NKG2D ligands, NY-ESO-1, oncofetal antigen (h5T4), PSCA, PSMA, VEGF-R2, and WT-1.

5. The method of claim 1, wherein the first and second tumor antigens are CD19 and CD10.

6. The method of claim 1, wherein the first and second tumor antigens are CD56 and CD138.

7. The method of claim 1, wherein the first and second tumor antigens are distinct antigens independently selected from the group consisting of mesothelin, folate receptor-a, CD44, and CD133.

8. The method of claim 1, wherein the first and second tumor antigens are PSCA and PSMA.

9. The method of claim 1, wherein the immunoresponsive cell is selected from the group consisting of a T cell, a Natural Killer (NK) cell, a pluripotent stem cell from which lymphoid cells may be differentiated, and combinations thereof.

10. The method of claim 1, wherein the immunoresponsive cell is a T cell.

11. The method of claim 10, wherein the T cell is selected from the group consisting of a cytotoxic T lymphocyte (CTL), a regulatory T cell, and combinations thereof.

12. The method of claim 1, wherein the intracellular signaling domain of the CAR comprises a CD32-chain signaling domain.

13. The method of claim 1, wherein the CCR comprises an intracellular signaling domain.

14. The method of claim 13, wherein the intracellular signaling domain of the CCR comprises a signaling domain of CD28 signaling domain, a signaling domain of 4-1BB, a signaling domain of CD97, a signaling domain of CD11a-CD18, a signaling domain of CD2, a signaling domain of ICOS, a signaling domain of CD27, a signaling domain of CD154, a signaling domain of CD5, or a signaling domain of OX40.

15. The method of claim 1, wherein the CAR binds to the first antigen with a dissociation constant (Kd) of about $1\times10^{-7}$ M or more.

16. The method of claim 1, wherein the CAR binds to the first antigen with a dissociation constant (Kd) of about $1\times10^{-6}$ M or more.

17. The method of claim 1, wherein the CAR binds to the first antigen with a binding affinity that is lower compared to the binding affinity with which the CCR binds to the second antigen.

18. A method of producing an immunoresponsive cell or a pharmaceutical composition comprising the immunoresponsive cell, the method comprising introducing into the immunoresponsive cell a nucleic acid molecule encoding:

a chimeric antigen receptor (CAR) that binds to a first antigen with a dissociation constant (Kd) of about $5\times10^{-8}$ M or more, wherein binding of the CAR to the first antigen is capable of delivering an activation signal to the immunoresponsive cell, and a chimeric co-stimulating receptor (CCR) that binds to a second antigen, wherein binding of the CCR to the second antigen is capable of delivering a costimulatory signal to the immunoresponsive cell but does not alone deliver an activation signal to the immunoresponsive cell;

wherein the immunoresponsive cell is capable of i) exhibiting negligible cytolytic activity against cells that are singly positive for the first antigen, and ii) inducing cytolytic activity against cells that are positive for both the first and second antigens.

* * * * *